US007112333B1

(12) United States Patent
Griffith et al.

(10) Patent No.: US 7,112,333 B1
(45) Date of Patent: *Sep. 26, 2006

(54) T CELL EPITOPES OF RYEGRASS POLLEN ALLERGEN

(75) Inventors: Irwin J. Griffith, Edmonton (CA); Mei-Chang Kuo, Palo Alto, CA (US); Mohammad Luqman, Acton, MA (US)

(73) Assignee: Heska Corporation, Loveland, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/737,904

(22) PCT Filed: Aug. 5, 1994

(86) PCT No.: PCT/US94/09024

§ 371 (c)(1),
(2), (4) Date: Nov. 20, 1996

(87) PCT Pub. No.: WO95/06728

PCT Pub. Date: Mar. 9, 1995

(51) Int. Cl.
*A61K 38/04* (2006.01)
*A61K 38/10* (2006.01)
*C07K 7/00* (2006.01)
*C07K 7/06* (2006.01)

(52) U.S. Cl. .............................. 424/275.1; 424/185.1; 424/275.1; 424/276.1; 514/2; 514/12; 514/13; 514/14; 514/15; 514/16; 514/885; 530/324; 530/325; 530/326; 530/327; 530/328; 530/329; 530/370; 530/868

(58) Field of Classification Search ............. 424/185.1, 424/275.1, 276.1; 514/2, 12, 13, 14, 15, 514/16, 885; 530/324, 325, 326, 327, 328, 530/329, 370, 868
See application file for complete search history.

(56) References Cited

U.S. PATENT DOCUMENTS 5,721,119 A * 2/1998 Singh et al. ............... 435/69.3

FOREIGN PATENT DOCUMENTS

| WO | WO 93/04174 | 3/1993 |
| WO | WO 94/04564 | 3/1994 |
| WO | WO 95/06728 | * 3/1995 |

OTHER PUBLICATIONS

Perez et al. J. Biol. Chem., 27:16210-16215, 1990.*
Hurtenbach, U. et al.,"Prevention of Autoimmune Diabetes in Non-Obese Diabetic Mice by Treatment with a Class II Major Histocompatibility Complex-blocking Peptide", *J. Exp. Med.*, vol. 177 pp. 1499-1504 (1993).
Klysner, S. et al.,"Group V Allergens in grass pollens: IV. Similarities in amino acid compositions and NH2-terminal sequences of the Group V allergens from *Lolium perenne, Poa pratensis* and *Dactylis glomerata*", *Clin. and Experimental Allergy*, vol. 22 pp. 491-497 (1992).
Matthiesen, F. et al.,"Group V allergens in grass pollens. II. Investigation of group V allergens in pollens from 10 grasses",*Clin. and Experimental Allergy*, vol. 21 pp. 309-320 (1991).
Roberts, A. et al.,"N-Terminal Amino Acid Sequence Homologies of Group V Grass Pollen Allergens", *Int. Arch. Allergy Immunol.*, vol. 98 pp. 178-180 (1992).
Singh, M. et al.,"Isolation of cDNA encoding a newly identified major allergenic protein of rye-grass pollen: Intracellular targeting to the amyloplast", *Proc. Natl. Acad. Sci.*, vol. 88 pp. 1384-1388 (1991).
van Ree, R. et al.,"Characterization with monoclonal and polyclonal antibodies of a new major allergen from grass pollen in the group I molecular weight range", *J. Allergy Clin. Immunol.*, vol. 83 No. 1, pp. 144-151 (1989).
Zhang, L. et al.,"Allergenic and Antigenic Cross-Reactivities of Group IX Grass Pollen Allergens", *Int. Arch. Allergy Immunol.*, vol. 96 pp. 28-34 (1991).

* cited by examiner

*Primary Examiner*—Ronald B. Schwadron
(74) *Attorney, Agent, or Firm*—Lahive & Cockfield, LLP

(57) ABSTRACT

The present invention provides isolated peptides of Lol p V, a major protein allergen of the species *Lolium perenne*. Therapeutic peptides within the scope of the invention comprise at least one T cell epitope, or preferably at least two T cell epitopes of a protein allergen of Lol p V. Diagnostic peptides within the scope of the invention bind IgE. The invention also provides modified peptides having similar or enhanced therapeutic properties or other desirable properties as the corresponding, naturally-occurring allergen or portion thereof. The invention further provides nucleic acid sequences coding for peptides of the invention. Use of the therapeutic compositions comprising one or more peptides of the invention in the manufacture of medicaments for treating sensitivity to Lol p V or an allergen immunologically related to Lol p V, or for general ryegrass sensitivity in an individual, is also provided. The invention also provides nucleic acid sequence coding for Dac g V protein allergen as well as the amino acid sequence of Dac g V protein allergen.

2 Claims, 20 Drawing Sheets

```
CGCTATCCCTCCCTCGTACAAACAAGAGCAGCAATGGCCGTCCAGAAGTACACG              60
                              M  A  V  Q  K  Y  T
                                            -25           -20
GTGGCTCTATTCCTCGCCGTGGCCCTCGTGGCGGGCCCGCTCCTACGCCGCTGAC             120
 V  A  L  F  L  A  V  A  L  V  A  G  P  A  A  S  Y  A  A  D
           -15                          -10                   1
GCCGGCTACACCCCCGCAGCCGCGGCCACCCCGGCTACTCCTGCTGCCACCCCGGCTGCG       180
 A  G  Y  T  P  A  A  A  T  P  A  T  P  A  A  T  P  A  A
                  5                        10                20
GCTGGAGGGAAGGCGACGACCGAGCAGAAGCTGCTGGAGGACGTCAACGCTGGCTTC          240
 A  G  G  K  A  T  T  D  E  Q  K  L  L  E  D  V  N  A  G  F
              25                        30                  40
AAGGCAGCCGTGGCCGCTGCCAACGCCCCCGGCCAAGATCTTCGAG                     300
 K  A  A  V  A  A  A  N  A  P  P  A  D  K  F  K  I  F  E
           45                        50                  55              60
GCCGCTTCTCCGAGTCCTCCAAGGGCCTGCTCGCCACCTCCGCCGCCAAGGCCCACCCGGC      360
 A  A  F  S  E  S  S  K  G  L  L  A  T  S  A  A  K  A  P  G
              65                        70                 75              80
CTCATCCCCAAGCTCGACACCGCCTACGACGTCGCCTACAAGGCCGTCGCCGAGGCCACC       420
 L  I  P  K  L  D  T  A  Y  D  V  A  Y  K  A  A  E  G  A  T
              85                        90                  95             100
CCCGAGGCCAAGTACGACGCCTTCGTCACTGCCCTCACCGAAGCGCTCCGCGTCATCGCC       480
 P  E  A  K  Y  D  A  F  V  T  A  L  T  E  A  L  R  V  I  A
              105                       110                115             120
GGCGCCCTCGAGGTCCACGCCGTCAAGCCCGCCACCGAGGAGGTCCCTGCTGCTAAGATC       540
 G  A  L  E  V  H  A  V  K  P  A  T  E  E  V  P  A  A  K  I
              125                       130                135             140
```

Fig. 1A

```
CCCACCGGTGAGCTGCAGATCGTTGACAAGATCGATGCTGCCTTCAAGATCGCAGCCACC       600
 P  T  G  E  L  Q  I  V  D  K  I  D  A  A  F  K  I  A  A  T
              145                 150                 155                 160
GCCGCCAACGCCGCCCCCACCAACGATAAGTTCACCGTCTTCGAGAGTGCCTTCAACAAG       660
 A  A  N  A  A  P  T  N  D  K  F  T  V  F  E  S  A  F  N  K
         165                 170                 175                 180
GCCCTCAATGAGTGCACGGGCGGCGCCTATGAGACCTACAAGTTCATCCCCTCCCTCGAG       720
 A  L  N  E  C  T  G  G  A  Y  E  T  Y  K  F  I  P  S  L  E
         185                 190                 195                 200
GCCGCGGTCAAGCAGGCCCTACGCCCGCCACCGTCGCCGCCGAGGTCAAGTACGCC       780
 A  A  V  K  Q  A  Y  A  A  T  V  A  A  P  E  V  K  Y  A
         205                 210                 215                 220
GTCTTTGAGGCCGCGCTGACCAAGGCCATCACCGCCGCTGACCCAGGCACAGAAGGCCGGC       840
 V  F  E  A  A  L  T  K  A  I  T  A  M  T  Q  A  Q  K  A  G
         225                 230                 235                 240
AAACCCGCTGCCGCCGCCGCCACCCGCGCTGCCACCGGCCGCAACCGCC       900
 K  P  A  A  A  A  T  R  A  A  T  V  A  T  G  A  A  T  A
         245                 250                 255                 260
GCCGGGGTGCTGCCACCGCGCTGGTGGCTACAAAGCCTGATCAGCTTGCTAATAT       960
 A  A  G  A  A  T  A  A  A  G  G  Y  K  A  *
         265                 270                 275
ACTACTGAACGTATGTATGTGCATGATCCGGCGGCGAGTGGTTTTGTTGATAATTAATC      1020
TTCGTTTTCGTTTCATGCAGCCGGATCGAGAGGGCTTGCATGCTTGTAATAATTCAATA      1080
TTTTTCATTTCTTTTTGAAATCTGTAAATCCCCATGACAAGTAGTGGGATCAAGTCGGCAT      1140
GTATCACCGTTGATGCGAGTTTAACGATGGGAGTTTATCAAAGAATTTATTATTAAAAA      1200
AAAAAAAAAAAAAAAAAAAAAAAAAAAAAAA                                    1229
```

Fig. 1B

```
LIX-1     ADAGYTXAAAATXATXAATX
LIX-1.1   ADAGYTPAAAATPATPAATP
LIX-2     ATXATXAATXAAAGGKATTD
LIX-2.1   ATPATPAATPAAAGGKATTD
LIX-3     AAAGGKATTDEQKLLEDVNA
LIX-4     EQKLLEDVNAGFKAAVAAAA
LIX-5     GFKAAVAAAANAPPADKFKI
LIX-6     NAPPADKFKIFEAAFSESSK
LIX-7     FEAAFSESSKGLLATSAAKA
LIX-8     GLLATSAAKAPGLIPKLDTA
LIX-9     PGLIPKLDTAYDVAYKAAEG
LIX-10    YDVAYKAAEGATPEAKYDAF
LIX-11    ATPEAKYDAFVTALTEALRV
LIX-12    VTALTEALRVIAGALEVHAV
LIX-13    IAGALEVHAVKPATEEVPAA
LIX-14    KPATEEVPAAKIPTGELQIV
LIX-15    KIPTGELQIVDKIDAAFKIA
LIX-16    DKIDAAFKIAATAANAAPTN
LIX-17    ATAANAAPTNDKFTVFESAF
LIX-18    DKFTVFESAFNKALNECTGG
LIX-19    NKALNECTGGAYETYKFIPS
LIX-20    AYETYKFIPSLEAAVKQAYA
LIX-21    LEAAVKQAYAATVAAAPEVK
LIX-22    ATVAAAPEVKYAVFEAALTK
LIX-23    YAVFEAALTKAITAMTQAQK
LIX-24    AITAMTQAQKAGKPAAAAAT
LIX-25    AGKPAAAAATGAATVATGAA
LIX-26    GAATVATGAATAAAGAATAA
LIX-27    TAAAGAATAAAGGYKA
```

X REPRESENTS HYDROXYPROLINE RESIDUE

Fig. 2

| PEPTIDE NAME | PEPTIDE SEQUENCE |
| --- | --- |
| LPI-1 | IAKVPPGPNITAEYGDKWLD |
| LPI-1.1 | IAKVXPGXNITAEYGDKWLD |
| LPI-2 | TAEYGDKWLDAKSTWYGKPT |
| LPI-3 | AKSTWYGKPTGAGPKDNGGA |
| LPI-4 | GAGPKDNGGACGYKNVDKAP |
| LPI-4.1 | GAGPKDNGGACGYKDVDKAP |
| LPI-5 | CGYKDVDKAPFNGMTGCGNT |
| LPI-6 | FNGMTGCGNTPIFKDGRGCG |
| LPI-7 | PIFKDGRGCGSCFEIKCTKP |
| LPI-8 | SCFEIKCTKPESCSGEAVTV |
| LPI-9 | ESCSGEAVTVTITDDNEEPI |
| LPI-10 | TITDDNEEPIAPYHFDLSGH |
| LPI-11 | APYHFDLSGHAFGSMADDGE |
| LPI-11.1 | APYHFDLSGHAFGSMAKKGE |
| LPI-12 | AFGSMADDGEEQKLRSAGEL |
| LPI-12.1 | AFGSMAKKGEEQKLRSAGEL |
| LPI-13 | EQKLRSAGELELQFRRVKCK |
| LPI-14 | ELQFRRVKCKYPDDTKPTFH |
| LPI-15 | YPDDTKPTFHVEKASNPNYL |
| LPI-16 | VEKASNPNYLAILVKYVDGD |
| LPI-16.1 | VEKGSNPNYLAILVKYVDGD |
| LPI-17 | AILVKYVDGDGDVVAVDIKE |
| LPI-18 | GDVVAVDIKEKGKDKWIELK |
| LPI-19 | KGKDKWIELKESWGAVWRID |
| LPI-20 | ESWGAVWRIDTPDKLTGPFT |
| LPI-21 | TPDKLTGPFTVRYTTEGGTK |
| LPI-22 | VRYTTEGGTKSEVEDVIPEG |
| LPI-23 | SEVEDVIPEGWKADTSYSAK |

Fig. 3

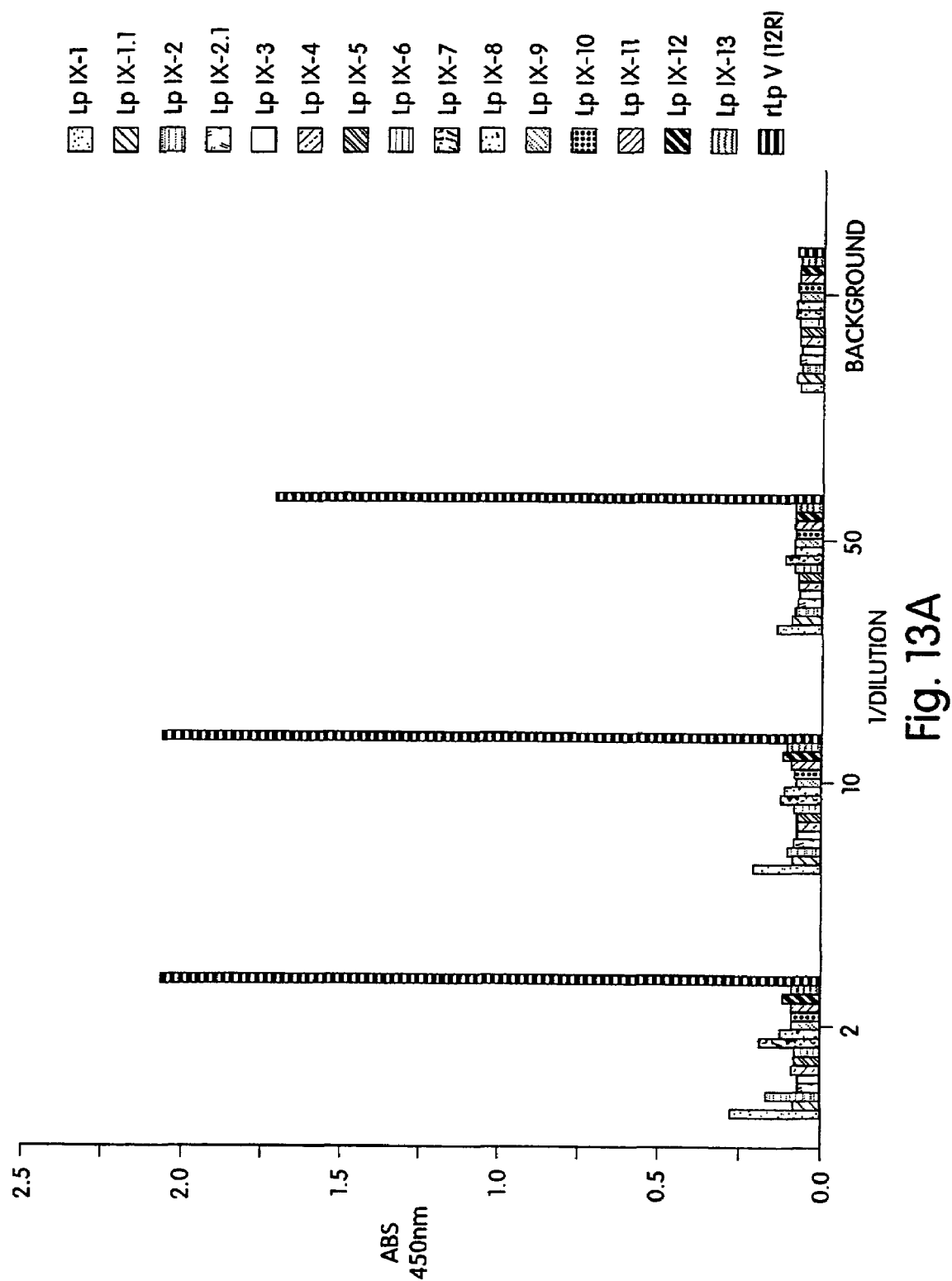

```
GAATTCGAGGATCCGGGTACCATGGCTCCGACAAACCAACGCAAGAGCAGCAATGCA           58
                                                 M  A
                                                -24

GTGCAGCAGTACACGGTGGCGCTGTTCCTGGCCGTGGCCTCGTGTCGGGCCCGCGCCTCC       118
 V  Q  Q  Y  T  V  A  L  F  L  A  V  A  S  C  R  A  R  A  S
   -20                                -10

TACGCCGCGACGCCGGCTACGCCCCGCCACTCCCGCCACCCCGGCTACCCCCGCGGCC         178
 Y  A  A  D  A  G  Y  A  P  A  T  P  A  T  P  A  T  P  A  A
                  1                                  10

CCAGGCGCAGCGGTGCCAGCAGGAAGGCGGACCGAGGAGCAGAAGCTGATCGAGAAG          238
 P  G  A  A  V  P  A  G  K  A  A  T  E  E  Q  K  L  I  E  K
    20                                30

ATCAACGCCGGCTTCAAGGCCGCCGTGGCCGCCGCCGGCGTCCCGCCAGGCGACAAG          298
 I  N  A  G  F  K  A  A  V  A  A  A  A  G  V  P  P  A  D  K
    40                                50

TACAAGACGTTCGTCGAAACCTTCGGCAAGGCCTCCAACAAGGCCTTCCTGGGGGACCTC       358
 Y  K  T  F  V  E  T  F  G  K  A  S  N  K  A  F  L  G  D  L
    60                                70

CCGACCAACTACGCCGATGTCAACTCCAGGGCCCAGCTCACCTCGAAGCTCGACGCCGCC      418
 P  T  N  Y  A  D  V  N  S  R  A  Q  L  T  S  K  L  D  A  A
    80                                90

TACAAGCTCGCCTACGACGCCGCCCAGGGCGCCACCCCCGAGGCCAAGTACGACGCCTAC      478
 Y  K  L  A  Y  D  A  A  Q  G  A  T  P  E  A  K  Y  D  A  Y
    100                               110
```

Fig. 16A

```
GTCGCCACCCTCAGCGAGGCGCTCCGCATCATCGCCGGCACCCTCGAGGTCCACGCCGTC   538
 V  A  T  L  S  E  A  L  R  I  I  A  G  T  L  E  V  H  A  V
            120                    130

AAGCCCGCTGCCGAGGAGGTCAAGCCTATCCCCGCCGGAGAGCTGCAGATCGTCGACAAG   598
 K  P  A  A  E  E  V  K  P  I  P  A  G  E  L  Q  I  V  D  K
        140                    150

ATTGACGTCGCCTTCAGAACTGCCGCCAACGCCGCCCCAACGACAAG   658
 I  D  V  A  F  R  T  A  A  T  A  A  N  A  A  P  T  N  D  K
            160                    170

TTCACCGTATTCGAGACCACCTTTAACAAGGCCATCAAGGAGAGCACGGGCGGCACCTAC   718
 F  T  V  F  E  T  T  F  N  K  A  I  K  E  S  T  G  G  T  Y
        180                    190

GAGAGCTACAAGTTCATTCCCACCCTTGAGGCCGCCGTTAAGCAGGCCTACGCCGCCACC   778
 E  S  Y  K  F  I  P  T  L  E  A  A  V  K  Q  A  Y  A  A  T
            200                    210

GTCGCGATCCGCGCCGGAGGTCAAGTACGCCGTCTCTTTGAGACCGCTGAAAAAGGCGGTC   838
 V  A  S  A  P  E  V  K  Y  A  V  F  E  T  A  L  K  K  A  V
        220                    230

ACCGCCATGTCCGAGGCCCAGAAGGAAGCCAAGCCCGCCACCGCCGACCCCCCACC   898
 T  A  M  S  E  A  Q  K  E  A  K  P  A  T  A  T  P  T  P  T
            240                    250
```

Fig. 16B

```
GCAACTGCCGCGGCGGTGGCCACCAACGCCCCCGTCGCTGGTGGCTACAAA    958
 A  T  A  A  A  V  A  T  N  A  A  P  V  A  A  G  Y  K
    260                         270
ATCTGATCAACTCGCTAGCAATATACACATCCATCATGCACATATAGAGCTGTGTATGTA   1018
 I  *
TGTGCATGCATGCCGTGGCCGCGCGCAAGTTGCTCATAATTAATTCTTGGTTTTCGTTG    1078
CTTGCATCCACGAGCGACCCGTGGATAGTCGCATGTGTATGTAATTTTTTCTGAG       1138
AAATGTGTATATGTAATATATAATTGAGTACTAAAAAAAAA                     1181
```

Fig. 16C

SEQUENCE LISTING

<160> NUMBER OF SEQ ID NOS: 62

<210> SEQ ID NO 1
<211> LENGTH: 1229
<212> TYPE: DNA

<213> ORGANISM: Lolium pernne
<220> FEATURE:
<221> NAME/KEY: CDS
<222> LOCATION: (40)...(942)
<220> FEATURE:
<221> NAME/KEY: sig_peptide
<222> LOCATION: (40)...(115)
<220> FEATURE:
<221> NAME/KEY: mat_peptide
<222> LOCATION: (115)...(942)

<400> SEQUENCE: 1

```
cgctatccct ccctcgtaca aacaaacgca agagcagca atg gcc gtc cag aag                54
                                            Met Ala Val Gln Lys
                                                    -25 tac acg gtg gct cta ttc ctc gcc gtg gcc ctc gtg gcg ggc ccg gcc              102
Tyr Thr Val Ala Leu Phe Leu Ala Val Ala Leu Val Ala Gly Pro Ala
-20             -15                 -10                  -5 gcc tcc tac gcc gct gac gcc ggc tac acc ccc gca gcc gcg gcc acc              150
Ala Ser Tyr Ala Ala Asp Ala Gly Tyr Thr Pro Ala Ala Ala Thr
         1               5                    10 ccg gct act cct gct gcc acc ccg gct gcg gct gga ggg aag gcg acg              198
Pro Ala Thr Pro Ala Ala Thr Pro Ala Ala Gly Gly Lys Ala Thr
        15                  20                  25 acc gac gag cag aag ctg ctg gag gac gtc aac gct ggc ttc aag gca              246
Thr Asp Glu Gln Lys Leu Leu Glu Asp Val Asn Ala Gly Phe Lys Ala
        30                  35                  40 gcc gtg gcc gcc gct gcc aac gcc cct ccg gcg gac aag ttc aag atc              294
Ala Val Ala Ala Ala Ala Asn Ala Pro Pro Ala Asp Lys Phe Lys Ile
45                  50                  55                  60 ttc gag gcc gcc ttc tcc gag tcc tcc aag ggc ctc ctc gcc acc tcc              342
Phe Glu Ala Ala Phe Ser Glu Ser Ser Lys Gly Leu Leu Ala Thr Ser
                65                  70                  75 gcc gcc aag gca ccc ggc ctc atc ccc aag ctc gac acc gcc tac gac              390
Ala Ala Lys Ala Pro Gly Leu Ile Pro Lys Leu Asp Thr Ala Tyr Asp
            80                  85                  90 gtc gcc tac aag gcc gcc gag ggc gcc acc ccc gag gcc aag tac gac              438
Val Ala Tyr Lys Ala Ala Glu Gly Ala Thr Pro Glu Ala Lys Tyr Asp
        95                  100                 105 gcc ttc gtc act gcc ctc acc gaa gcg ctc cgc gtc atc gcc ggc gcc              486
Ala Phe Val Thr Ala Leu Thr Glu Ala Leu Arg Val Ile Ala Gly Ala
    110                 115                 120 ctc gag gtc cac gcc gtc aag ccc gcc acc gag gag gtc cct gct gct              534
Leu Glu Val His Ala Val Lys Pro Ala Thr Glu Glu Val Pro Ala Ala
125                 130                 135                 140 aag atc ccc acc ggt gag ctg cag atc gtt gac aag atc gat gct gcc              582
Lys Ile Pro Thr Gly Glu Leu Gln Ile Val Asp Lys Ile Asp Ala Ala
                145                 150                 155 ttc aag atc gca gcc acc gcc gcc aac gcc gcc ccc acc aac gat aag              630
Phe Lys Ile Ala Ala Thr Ala Ala Asn Ala Ala Pro Thr Asn Asp Lys
            160                 165                 170 ttc acc gtc ttc gag agt gcc ttc aac aag gcc ctc aat gag tgc acg              678
Phe Thr Val Phe Glu Ser Ala Phe Asn Lys Ala Leu Asn Glu Cys Thr
        175                 180                 185 ggc ggc gcc tat gag acc tac aag ttc atc ccc tcc ctc gag gcc gcg              726
Gly Gly Ala Tyr Glu Thr Tyr Lys Phe Ile Pro Ser Leu Glu Ala Ala
    190                 195                 200 gtc aag cag gcc tac gcc gcc acc gtc gcc gcc gcg ccc gag gtc aag              774
Val Lys Gln Ala Tyr Ala Ala Thr Val Ala Ala Ala Pro Glu Val Lys
205                 210                 215                 220 tac gcc gtc ttt gag gcc gcg ctg acc aag gcc atc acc gcc atg acc              822
Tyr Ala Val Phe Glu Ala Ala Leu Thr Lys Ala Ile Thr Ala Met Thr
```

-continued

```
                     225                 230                 235
cag gca cag aag gcc ggc aaa ccc gct gcc gcc gct gcc aca ggc gcc    870
Gln Ala Gln Lys Ala Gly Lys Pro Ala Ala Ala Ala Ala Thr Gly Ala
            240                 245                 250 gca acc gtt gcc acc ggc gcc gca acc gcc gcc gcc ggt gct gcc acc    918
Ala Thr Val Ala Thr Gly Ala Ala Thr Ala Ala Ala Gly Ala Ala Thr
                255                 260                 265 gcc gct gct ggt ggc tac aaa gcc tgatcagctt gctaatatac tactgaacgt   972
Ala Ala Ala Gly Gly Tyr Lys Ala
        270                 275 atgtatgtgc atgatccggg cggcgagtgg ttttgttgat aattaatctt cgttttcgtt  1032
tcatgcagcc gcgatcgaga gggcttgcat gcttgtaata attcaatatt tttcatttct  1092
ttttgaatct gtaaatcccc atgacaagta gtgggatcaa gtcggcatgt atcaccgttg  1152
atgcgagttt aacgatgggg agtttatcaa agaatttatt attaaaaaaa aaaaaaaaa   1212 aaaaaaaaaa aaaaaa                                                  1229
```

<210> SEQ ID NO 2
<211> LENGTH: 301
<212> TYPE: PRT
<213> ORGANISM: Lolium pernne
<220> FEATURE:
<221> NAME/KEY: SIGNAL
<222> LOCATION: (1)...(25)

<400> SEQUENCE: 2

```
Met Ala Val Gln Lys Tyr Thr Val Ala Leu Phe Leu Ala Val Ala Leu
-25                 -20                 -15                 -10

Val Ala Gly Pro Ala Ala Ser Tyr Ala Ala Asp Ala Gly Tyr Thr Pro
                -5                  1               5

Ala Ala Ala Ala Thr Pro Ala Thr Pro Ala Ala Thr Pro Ala Ala Ala
            10                  15                  20

Gly Gly Lys Ala Thr Thr Asp Glu Gln Lys Leu Leu Glu Asp Val Asn
        25                  30                  35

Ala Gly Phe Lys Ala Ala Val Ala Ala Ala Asn Ala Pro Pro Ala
40                  45                  50                  55

Asp Lys Phe Lys Ile Phe Glu Ala Ala Phe Ser Glu Ser Lys Gly
                60                  65                  70

Leu Leu Ala Thr Ser Ala Ala Lys Ala Pro Gly Leu Ile Pro Lys Leu
                75                  80                  85

Asp Thr Ala Tyr Asp Val Ala Tyr Lys Ala Ala Glu Gly Ala Thr Pro
            90                  95                  100

Glu Ala Lys Tyr Asp Ala Phe Val Thr Ala Leu Thr Glu Ala Leu Arg
        105                 110                 115

Val Ile Ala Gly Ala Leu Glu Val His Ala Val Lys Pro Ala Thr Glu
120                 125                 130                 135

Glu Val Pro Ala Ala Lys Ile Pro Thr Gly Glu Leu Gln Ile Val Asp
                140                 145                 150

Lys Ile Asp Ala Ala Phe Lys Ile Ala Ala Thr Ala Ala Asn Ala Ala
                155                 160                 165

Pro Thr Asn Asp Lys Phe Thr Val Phe Glu Ser Ala Phe Asn Lys Ala
            170                 175                 180

Leu Asn Glu Cys Thr Gly Gly Ala Tyr Glu Thr Tyr Lys Phe Ile Pro
        185                 190                 195

Ser Leu Glu Ala Ala Val Lys Gln Ala Tyr Ala Ala Thr Val Ala Ala
200                 205                 210                 215
```

-continued

```
Ala Pro Glu Val Lys Tyr Ala Val Phe Glu Ala Ala Leu Thr Lys Ala
                220                 225                 230

Ile Thr Ala Met Thr Gln Ala Gln Lys Ala Gly Lys Pro Ala Ala Ala
                235                 240                 245

Ala Ala Thr Gly Ala Ala Thr Val Ala Thr Gly Ala Ala Thr Ala Ala
                250                 255                 260

Ala Gly Ala Ala Thr Ala Ala Gly Gly Tyr Lys Ala
                265                 270                 275

<210> SEQ ID NO 3
<211> LENGTH: 20
<212> TYPE: PRT
<213> ORGANISM: Lolium perenne
<220> FEATURE:
<221> NAME/KEY: VARIANT
<222> LOCATION: (7)
<223> OTHER INFORMATION: Xaa = hydroxyproline residue
<220> FEATURE:
<221> NAME/KEY: VARIANT
<222> LOCATION: (13)
<223> OTHER INFORMATION: Xaa = hydroxyproline residue
<220> FEATURE:
<221> NAME/KEY: VARIANT
<222> LOCATION: (16)
<223> OTHER INFORMATION: Xaa = hydroxyproline residue
<220> FEATURE:
<221> NAME/KEY: VARIANT
<222> LOCATION: (20)
<223> OTHER INFORMATION: Xaa = hydroxyproline residue

<400> SEQUENCE: 3

Ala Asp Ala Gly Tyr Thr Xaa Ala Ala Ala Thr Xaa Ala Thr Xaa
  1               5                  10                  15

Ala Ala Thr Xaa
            20

<210> SEQ ID NO 4
<211> LENGTH: 20
<212> TYPE: PRT
<213> ORGANISM: Lolium perenne
<220> FEATURE:
<221> NAME/KEY: VARIANT
<222> LOCATION: (3)
<223> OTHER INFORMATION: Xaa = hydroxyproline residue
<220> FEATURE:
<221> NAME/KEY: VARIANT
<222> LOCATION: (6)
<223> OTHER INFORMATION: Xaa = hydroxyproline residue
<220> FEATURE:
<221> NAME/KEY: VARIANT
<222> LOCATION: (10)
<223> OTHER INFORMATION: Xaa = hydroxyproline residue

<400> SEQUENCE: 4

Ala Thr Xaa Ala Thr Xaa Ala Ala Thr Xaa Ala Ala Ala Gly Gly Lys
  1               5                  10                  15

Ala Thr Thr Asp
            20

<210> SEQ ID NO 5
<211> LENGTH: 20
<212> TYPE: PRT
<213> ORGANISM: Lolium perenne
<220> FEATURE:

<400> SEQUENCE: 5

Ala Ala Ala Gly Gly Lys Ala Thr Thr Asp Glu Gln Lys Leu Leu Glu
```

-continued

```
                1               5                  10                 15
Asp Val Asn Ala
            20

<210> SEQ ID NO 6
<211> LENGTH: 20
<212> TYPE: PRT
<213> ORGANISM: Lolium perenne

<400> SEQUENCE: 6

Glu Gln Lys Leu Leu Glu Asp Val Asn Ala Gly Phe Lys Ala Ala Val
 1               5                  10                  15

Ala Ala Ala Ala
            20

<210> SEQ ID NO 7
<211> LENGTH: 20
<212> TYPE: PRT
<213> ORGANISM: Lolium perenne

<400> SEQUENCE: 7

Gly Phe Lys Ala Ala Val Ala Ala Ala Asn Ala Pro Pro Ala Asp
 1               5                  10                  15

Lys Phe Lys Ile
            20

<210> SEQ ID NO 8
<211> LENGTH: 20
<212> TYPE: PRT
<213> ORGANISM: Lolium perenne

<400> SEQUENCE: 8

Asn Ala Pro Pro Ala Asp Lys Phe Lys Ile Phe Glu Ala Ala Phe Ser
 1               5                  10                  15

Glu Ser Ser Lys
            20

<210> SEQ ID NO 9
<211> LENGTH: 20
<212> TYPE: PRT
<213> ORGANISM: Lolium perenne

<400> SEQUENCE: 9

Phe Glu Ala Ala Phe Ser Glu Ser Ser Lys Gly Leu Leu Ala Thr Ser
 1               5                  10                  15

Ala Ala Lys Ala
            20

<210> SEQ ID NO 10
<211> LENGTH: 20
<212> TYPE: PRT
<213> ORGANISM: Lolium perenne

<400> SEQUENCE: 10

Gly Leu Leu Ala Thr Ser Ala Ala Lys Ala Pro Gly Leu Ile Pro Lys
 1               5                  10                  15

Leu Asp Thr Ala
            20

<210> SEQ ID NO 11
<211> LENGTH: 20
<212> TYPE: PRT
```

```
<213> ORGANISM: Lolium perenne

<400> SEQUENCE: 11

Pro Gly Leu Ile Pro Lys Leu Asp Thr Ala Tyr Asp Val Ala Tyr Lys
 1               5                  10                  15

Ala Ala Glu Gly
            20

<210> SEQ ID NO 12
<211> LENGTH: 20
<212> TYPE: PRT
<213> ORGANISM: Lolium perenne

<400> SEQUENCE: 12

Tyr Asp Val Ala Tyr Lys Ala Ala Glu Gly Ala Thr Pro Glu Ala Lys
 1               5                  10                  15

Tyr Asp Ala Phe
            20

<210> SEQ ID NO 13
<211> LENGTH: 20
<212> TYPE: PRT
<213> ORGANISM: Lolium perenne

<400> SEQUENCE: 13

Ala Thr Pro Glu Ala Lys Tyr Asp Ala Phe Val Thr Ala Leu Thr Glu
 1               5                  10                  15

Ala Leu Arg Val
            20

<210> SEQ ID NO 14
<211> LENGTH: 20
<212> TYPE: PRT
<213> ORGANISM: Lolium perenne

<400> SEQUENCE: 14

Val Thr Ala Leu Thr Glu Ala Leu Arg Val Ile Ala Gly Ala Leu Glu
 1               5                  10                  15

Val His Ala Val
            20

<210> SEQ ID NO 15
<211> LENGTH: 20
<212> TYPE: PRT
<213> ORGANISM: Lolium perenne

<400> SEQUENCE: 15

Ile Ala Gly Ala Leu Glu Val His Ala Val Lys Pro Ala Thr Glu Glu
 1               5                  10                  15

Val Pro Ala Ala
            20

<210> SEQ ID NO 16
<211> LENGTH: 20
<212> TYPE: PRT
<213> ORGANISM: Lolium perenne

<400> SEQUENCE: 16

Lys Pro Ala Thr Glu Glu Val Pro Ala Ala Lys Ile Pro Thr Gly Glu
 1               5                  10                  15

Leu Gln Ile Val
            20
```

```
<210> SEQ ID NO 17
<211> LENGTH: 20
<212> TYPE: PRT
<213> ORGANISM: Lolium perenne

<400> SEQUENCE: 17

Lys Ile Pro Thr Gly Glu Leu Gln Ile Val Asp Lys Ile Asp Ala Ala
 1               5                  10                  15

Phe Lys Ile Ala
            20

<210> SEQ ID NO 18
<211> LENGTH: 20
<212> TYPE: PRT
<213> ORGANISM: Lolium perenne

<400> SEQUENCE: 18

Asp Lys Ile Asp Ala Ala Phe Lys Ile Ala Ala Thr Ala Ala Asn Ala
 1               5                  10                  15

Ala Pro Thr Asn
            20

<210> SEQ ID NO 19
<211> LENGTH: 20
<212> TYPE: PRT
<213> ORGANISM: Lolium perenne

<400> SEQUENCE: 19

Ala Thr Ala Ala Asn Ala Ala Pro Thr Asn Asp Lys Phe Thr Val Phe
 1               5                  10                  15

Glu Ser Ala Phe
            20

<210> SEQ ID NO 20
<211> LENGTH: 20
<212> TYPE: PRT
<213> ORGANISM: Lolium perenne

<400> SEQUENCE: 20

Asp Lys Phe Thr Val Phe Glu Ser Ala Phe Asn Lys Ala Leu Asn Glu
 1               5                  10                  15

Cys Thr Gly Gly
            20

<210> SEQ ID NO 21
<211> LENGTH: 20
<212> TYPE: PRT
<213> ORGANISM: Lolium perenne

<400> SEQUENCE: 21

Asn Lys Ala Leu Asn Glu Cys Thr Gly Gly Ala Tyr Glu Thr Tyr Lys
 1               5                  10                  15

Phe Ile Pro Ser
            20

<210> SEQ ID NO 22
<211> LENGTH: 20
<212> TYPE: PRT
<213> ORGANISM: Lolium perenne

<400> SEQUENCE: 22
```

-continued

```
Ala Tyr Glu Thr Tyr Lys Phe Ile Pro Ser Leu Glu Ala Ala Val Lys
 1               5                  10                  15

Gln Ala Tyr Ala
            20

<210> SEQ ID NO 23
<211> LENGTH: 20
<212> TYPE: PRT
<213> ORGANISM: Lolium perenne

<400> SEQUENCE: 23

Leu Glu Ala Ala Val Lys Gln Ala Tyr Ala Ala Thr Val Ala Ala Ala
 1               5                  10                  15

Pro Glu Val Lys
            20

<210> SEQ ID NO 24
<211> LENGTH: 20
<212> TYPE: PRT
<213> ORGANISM: Lolium perenne

<400> SEQUENCE: 24

Ala Thr Val Ala Ala Ala Pro Glu Val Lys Tyr Ala Val Phe Glu Ala
 1               5                  10                  15

Ala Leu Thr Lys
            20

<210> SEQ ID NO 25
<211> LENGTH: 20
<212> TYPE: PRT
<213> ORGANISM: Lolium perenne

<400> SEQUENCE: 25

Tyr Ala Val Phe Glu Ala Ala Leu Thr Lys Ala Ile Thr Ala Met Thr
 1               5                  10                  15

Gln Ala Gln Lys
            20

<210> SEQ ID NO 26
<211> LENGTH: 20
<212> TYPE: PRT
<213> ORGANISM: Lolium perenne

<400> SEQUENCE: 26

Ala Ile Thr Ala Met Thr Gln Ala Gln Lys Ala Gly Lys Pro Ala Ala
 1               5                  10                  15

Ala Ala Ala Thr
            20

<210> SEQ ID NO 27
<211> LENGTH: 20
<212> TYPE: PRT
<213> ORGANISM: Lolium perenne

<400> SEQUENCE: 27

Ala Gly Lys Pro Ala Ala Ala Ala Thr Gly Ala Ala Thr Val Ala
 1               5                  10                  15

Thr Gly Ala Ala
            20

<210> SEQ ID NO 28
<211> LENGTH: 20
```

```
<212> TYPE: PRT
<213> ORGANISM: Lolium perenne

<400> SEQUENCE: 28

Gly Ala Ala Thr Val Ala Thr Gly Ala Ala Thr Ala Ala Ala Gly Ala
 1               5                  10                  15

Ala Thr Ala Ala
            20

<210> SEQ ID NO 29
<211> LENGTH: 16
<212> TYPE: PRT
<213> ORGANISM: Lolium perenne

<400> SEQUENCE: 29

Thr Ala Ala Ala Gly Ala Ala Thr Ala Ala Ala Gly Gly Tyr Lys Ala
 1               5                  10                  15

<210> SEQ ID NO 30
<211> LENGTH: 20
<212> TYPE: PRT
<213> ORGANISM: Lolium perenne

<400> SEQUENCE: 30

Ile Ala Lys Val Pro Pro Gly Pro Asn Ile Thr Ala Glu Tyr Gly Asp
 1               5                  10                  15

Lys Trp Leu Asp
            20

<210> SEQ ID NO 31
<211> LENGTH: 20
<212> TYPE: PRT
<213> ORGANISM: Lolium perenne
<220> FEATURE:
<221> NAME/KEY: VARIANT
<222> LOCATION: (5)
<223> OTHER INFORMATION: Xaa = hydroxyproline
<220> FEATURE:
<221> NAME/KEY: VARIANT
<222> LOCATION: (8)
<223> OTHER INFORMATION: Xaa = hydroxyproline

<400> SEQUENCE: 31

Ile Ala Lys Val Xaa Pro Gly Xaa Asn Ile Thr Ala Glu Tyr Gly Asp
 1               5                  10                  15

Lys Trp Leu Asp
            20

<210> SEQ ID NO 32
<211> LENGTH: 20
<212> TYPE: PRT
<213> ORGANISM: Lolium perenne

<400> SEQUENCE: 32

Thr Ala Glu Tyr Gly Asp Lys Trp Leu Asp Ala Lys Ser Thr Trp Tyr
 1               5                  10                  15

Gly Lys Pro Thr
            20

<210> SEQ ID NO 33
<211> LENGTH: 20
<212> TYPE: PRT
<213> ORGANISM: Lolium perenne

<400> SEQUENCE: 33
```

-continued

Gly Ala Gly Pro Lys Asp Asn Gly Gly Ala Cys Gly Tyr Lys Asn Val
 1               5                  10                  15

Asp Lys Ala Pro
            20

<210> SEQ ID NO 34
<211> LENGTH: 20
<212> TYPE: PRT
<213> ORGANISM: Lolium perenne

<400> SEQUENCE: 34

Gly Ala Gly Pro Lys Asp Asn Gly Gly Ala Cys Gly Tyr Lys Asp Val
 1               5                  10                  15

Asp Lys Ala Pro
            20

<210> SEQ ID NO 35
<211> LENGTH: 20
<212> TYPE: PRT
<213> ORGANISM: Lolium perenne

<400> SEQUENCE: 35

Cys Gly Tyr Lys Asp Val Asp Lys Ala Pro Phe Asn Gly Met Thr Gly
 1               5                  10                  15

Cys Gly Asn Thr
            20

<210> SEQ ID NO 36
<211> LENGTH: 20
<212> TYPE: PRT
<213> ORGANISM: Lolium perenne

<400> SEQUENCE: 36

Phe Asn Gly Met Thr Gly Cys Gly Asn Thr Pro Ile Phe Lys Asp Gly
 1               5                  10                  15

Arg Gly Cys Gly
            20

<210> SEQ ID NO 37
<211> LENGTH: 20
<212> TYPE: PRT
<213> ORGANISM: Lolium perenne

<400> SEQUENCE: 37

Pro Ile Phe Lys Asp Gly Arg Gly Cys Gly Ser Cys Phe Glu Ile Lys
 1               5                  10                  15

Cys Thr Lys Pro
            20

<210> SEQ ID NO 38
<211> LENGTH: 20
<212> TYPE: PRT
<213> ORGANISM: Lolium perenne

<400> SEQUENCE: 38

Ser Cys Phe Glu Ile Lys Cys Thr Lys Pro Glu Ser Cys Ser Gly Glu
 1               5                  10                  15

Ala Val Thr Val
            20

<210> SEQ ID NO 39

```
<211> LENGTH: 20
<212> TYPE: PRT
<213> ORGANISM: Lolium perenne

<400> SEQUENCE: 39

Glu Ser Cys Ser Gly Glu Ala Val Thr Val Thr Ile Thr Asp Asp Asn
 1               5                  10                  15

Glu Glu Pro Ile
            20

<210> SEQ ID NO 40
<211> LENGTH: 20
<212> TYPE: PRT
<213> ORGANISM: Lolium perenne

<400> SEQUENCE: 40

Thr Ile Thr Asp Asp Asn Glu Glu Pro Ile Ala Pro Tyr His Phe Asp
 1               5                  10                  15

Leu Ser Gly His
            20

<210> SEQ ID NO 41
<211> LENGTH: 20
<212> TYPE: PRT
<213> ORGANISM: Lolium perenne

<400> SEQUENCE: 41

Ala Pro Tyr His Phe Asp Leu Ser Gly His Ala Phe Gly Ser Met Ala
 1               5                  10                  15

Asp Asp Gly Glu
            20

<210> SEQ ID NO 42
<211> LENGTH: 20
<212> TYPE: PRT
<213> ORGANISM: Lolium perenne

<400> SEQUENCE: 42

Ala Phe Gly Ser Met Ala Asp Asp Gly Glu Glu Gln Lys Leu Arg Ser
 1               5                  10                  15

Ala Gly Glu Leu
            20

<210> SEQ ID NO 43
<211> LENGTH: 20
<212> TYPE: PRT
<213> ORGANISM: Lolium perenne

<400> SEQUENCE: 43

Glu Gln Lys Leu Arg Ser Ala Gly Glu Leu Glu Leu Gln Phe Arg Arg
 1               5                  10                  15

Val Lys Cys Lys
            20

<210> SEQ ID NO 44
<211> LENGTH: 20
<212> TYPE: PRT
<213> ORGANISM: Lolium perenne

<400> SEQUENCE: 44

Glu Leu Gln Phe Arg Arg Val Lys Cys Lys Tyr Pro Asp Asp Thr Lys
 1               5                  10                  15
```

Pro Thr Phe His
            20

<210> SEQ ID NO 45
<211> LENGTH: 20
<212> TYPE: PRT
<213> ORGANISM: Lolium perenne

<400> SEQUENCE: 45

Tyr Pro Asp Asp Thr Lys Pro Thr Phe His Val Glu Lys Ala Ser Asn
 1               5                  10                  15

Pro Asn Tyr Leu
            20

<210> SEQ ID NO 46
<211> LENGTH: 20
<212> TYPE: PRT
<213> ORGANISM: Lolium perenne

<400> SEQUENCE: 46

Val Glu Lys Ala Ser Asn Pro Asn Tyr Leu Ala Ile Leu Val Lys Tyr
 1               5                  10                  15

Val Asp Gly Asp
            20

<210> SEQ ID NO 47
<211> LENGTH: 20
<212> TYPE: PRT
<213> ORGANISM: Lolium perenne

<400> SEQUENCE: 47

Val Glu Lys Gly Ser Asn Pro Asn Tyr Leu Ala Ile Leu Val Lys Tyr
 1               5                  10                  15

Val Asp Gly Asp
            20

<210> SEQ ID NO 48
<211> LENGTH: 20
<212> TYPE: PRT
<213> ORGANISM: Lolium perenne

<400> SEQUENCE: 48

Ala Ile Leu Val Lys Tyr Val Asp Gly Asp Gly Asp Val Val Ala Val
 1               5                  10                  15

Asp Ile Lys Glu
            20

<210> SEQ ID NO 49
<211> LENGTH: 20
<212> TYPE: PRT
<213> ORGANISM: Lolium perenne

<400> SEQUENCE: 49

Gly Asp Val Val Ala Val Asp Ile Lys Glu Lys Gly Lys Asp Lys Trp
 1               5                  10                  15

Ile Glu Leu Lys
            20

<210> SEQ ID NO 50
<211> LENGTH: 20
<212> TYPE: PRT
<213> ORGANISM: Lolium perenne -continued

```
<400> SEQUENCE: 50

Lys Gly Lys Asp Lys Trp Ile Glu Leu Lys Glu Ser Trp Gly Ala Val
 1               5                  10                  15

Trp Arg Ile Asp
            20

<210> SEQ ID NO 51
<211> LENGTH: 20
<212> TYPE: PRT
<213> ORGANISM: Lolium perenne

<400> SEQUENCE: 51

Thr Pro Asp Lys Leu Thr Gly Pro Phe Thr Val Arg Tyr Thr Thr Glu
 1               5                  10                  15

Gly Gly Thr Lys
            20

<210> SEQ ID NO 52
<211> LENGTH: 20
<212> TYPE: PRT
<213> ORGANISM: Lolium perenne

<400> SEQUENCE: 52

Val Arg Tyr Thr Thr Glu Gly Gly Thr Lys Ser Glu Val Glu Asp Val
 1               5                  10                  15

Ile Pro Glu Gly
            20

<210> SEQ ID NO 53
<211> LENGTH: 20
<212> TYPE: PRT
<213> ORGANISM: Lolium perenne

<400> SEQUENCE: 53

Ser Glu Val Glu Asp Val Ile Pro Glu Gly Trp Lys Ala Asp Thr Ser
 1               5                  10                  15

Tyr Ser Ala Lys
            20

<210> SEQ ID NO 54
<211> LENGTH: 33
<212> TYPE: PRT
<213> ORGANISM: Lolium perenne
<220> FEATURE:
<221> NAME/KEY: VARIANT
<222> LOCATION: (7)
<223> OTHER INFORMATION: Xaa = hydroxyproline residue
<220> FEATURE:
<221> NAME/KEY: VARIANT
<222> LOCATION: (13)
<223> OTHER INFORMATION: Xaa = hydroxyproline residue
<220> FEATURE:
<221> NAME/KEY: VARIANT
<222> LOCATION: (16)
<223> OTHER INFORMATION: Xaa = hydroxyproline residue
<220> FEATURE:
<221> NAME/KEY: VARIANT
<222> LOCATION: (20)
<223> OTHER INFORMATION: Xaa = hydroxyproline residue

<400> SEQUENCE: 54

Ala Asp Ala Gly Tyr Thr Xaa Ala Ala Ala Thr Xaa Ala Thr Xaa
 1               5                  10                  15

Ala Ala Thr Xaa Ala Ala Ala Gly Gly Lys Ala Thr Thr Asp Glu Gln
            20                  25                  30
```

Lys

<210> SEQ ID NO 55
<211> LENGTH: 20
<212> TYPE: PRT
<213> ORGANISM: Lolium perenne

<400> SEQUENCE: 55

Ala Lys Ser Thr Trp Tyr Gly Lys Pro Thr Gly Ala Gly Pro Lys Asp
 1               5                  10                  15

Asn Gly Gly Ala
            20

<210> SEQ ID NO 56
<211> LENGTH: 20
<212> TYPE: PRT
<213> ORGANISM: Lolium perenne

<400> SEQUENCE: 56

Glu Ser Trp Gly Ala Val Trp Arg Ile Asp Thr Pro Asp Lys Leu Thr
 1               5                  10                  15

Gly Pro Phe Thr
            20

<210> SEQ ID NO 57
<211> LENGTH: 1181
<212> TYPE: DNA
<213> ORGANISM: Lolium perenne
<220> FEATURE:
<221> NAME/KEY: CDS
<222> LOCATION: (53)..(961)
<220> FEATURE:
<221> NAME/KEY: mat_peptide
<222> LOCATION: (125)

<400> SEQUENCE: 57

```
gaattcgagg atccgggtac catggctccg acaaaccaac gcaagagcag ca atg gca       58
                                                          Met Ala gtg cag cag tac acg gtg gcg ctg ttc ctg gcc gtg gcc tcg tgt cgg        106
Val Gln Gln Tyr Thr Val Ala Leu Phe Leu Ala Val Ala Ser Cys Arg
    -20                 -15                 -10 gcc cgc gcc tcc tac gcc gcc gac gcc ggc tac gcc ccc gcc act ccc        154
Ala Arg Ala Ser Tyr Ala Ala Asp Ala Gly Tyr Ala Pro Ala Thr Pro
 -5              -1   1               5                  10 gcc acc ccg gct acc ccc gcg gcc cca ggc gca gcg gtg cca gca ggg        202
Ala Thr Pro Ala Thr Pro Ala Ala Pro Gly Ala Ala Val Pro Ala Gly
                15                  20                  25 aag gcg gcg acc gag gag cag aag ctg atc gag aag atc aac gcc ggc        250
Lys Ala Ala Thr Glu Glu Gln Lys Leu Ile Glu Lys Ile Asn Ala Gly
                30                  35                  40 ttc aag gcc gcc gtg gcg gcc gcc gcg ggc gtc ccg cca ggc gac aag        298
Phe Lys Ala Ala Val Ala Ala Ala Ala Gly Val Pro Pro Gly Asp Lys
            45                  50                  55 tac aag acg ttc gtc gaa acc ttc ggc aag gcc tcc aac aag gcc ttc        346
Tyr Lys Thr Phe Val Glu Thr Phe Gly Lys Ala Ser Asn Lys Ala Phe
        60                  65                  70 ctg ggg gac ctc ccg acc aac tac gcc gat gtc aac tcc agg gcc cag        394
Leu Gly Asp Leu Pro Thr Asn Tyr Ala Asp Val Asn Ser Arg Ala Gln
75                  80                  85                  90 ctc acc tcg aag ctc gac gcc gcc tac aag ctc gcc tac gac gcc gcc        442
Leu Thr Ser Lys Leu Asp Ala Ala Tyr Lys Leu Ala Tyr Asp Ala Ala
                95                  100                 105
```

-continued

```
cag ggc gcc acc ccc gag gcc aag tac gac gcc tac gtc gcc acc ctc       490
Gln Gly Ala Thr Pro Glu Ala Lys Tyr Asp Ala Tyr Val Ala Thr Leu
            110                 115                 120 agc gag gcg ctc cgc atc atc gcc ggc acc ctc gag gtc cac gcc gtc       538
Ser Glu Ala Leu Arg Ile Ile Ala Gly Thr Leu Glu Val His Ala Val
        125                 130                 135 aag ccc gct gcc gag gag gtc aag cct atc ccc gcc gga gag ctg cag       586
Lys Pro Ala Ala Glu Glu Val Lys Pro Ile Pro Ala Gly Glu Leu Gln
140                 145                 150 atc gtc gac aag att gac gtc gcc ttc aga act gcc gcc acc gcc gcc       634
Ile Val Asp Lys Ile Asp Val Ala Phe Arg Thr Ala Ala Thr Ala Ala
155                 160                 165                 170 aac gcc gcc ccc acc aac gac aag ttc acc gta ttc gag acc acc ttt       682
Asn Ala Ala Pro Thr Asn Asp Lys Phe Thr Val Phe Glu Thr Thr Phe
                175                 180                 185 aac aag gcc atc aag gag agc acg ggc ggc acc tac gag agc tac aag       730
Asn Lys Ala Ile Lys Glu Ser Thr Gly Gly Thr Tyr Glu Ser Tyr Lys
            190                 195                 200 ttc att ccc acc ctt gag gcc gcc gtt aag cag gcc tac gcc gcc acc       778
Phe Ile Pro Thr Leu Glu Ala Ala Val Lys Gln Ala Tyr Ala Ala Thr
        205                 210                 215 gtc gca tcc gcg ccg gag gtc aag tac gcc gtc ttt gag acc gcg ctg       826
Val Ala Ser Ala Pro Glu Val Lys Tyr Ala Val Phe Glu Thr Ala Leu
    220                 225                 230 aaa aag gcg gtc acc gcc atg tcc gag gcc cag aag gaa gcc aag ccc       874
Lys Lys Ala Val Thr Ala Met Ser Glu Ala Gln Lys Glu Ala Lys Pro
235                 240                 245                 250 gcc acc gcc acc ccg acc ccc acc gca act gcc gcg gcc gcg gtg gcc       922
Ala Thr Ala Thr Pro Thr Pro Thr Ala Thr Ala Ala Ala Ala Val Ala
                255                 260                 265 acc aac gcc gcc ccc gtc gct gct ggt ggc tac aaa atc tgatcaactc       971
Thr Asn Ala Ala Pro Val Ala Ala Gly Gly Tyr Lys Ile
            270                 275 gctagcaata tacacatcca tcatgcacat atagagctgt gtatgtatgt gcatgcatgc      1031
cgtggcgccg cgcaagtttg ctcataatta attcttggtt ttcgttgctt gcatccacga      1091
gcgaccgagc ccgtggatag tcgcatgtgt atgtaatttt ttctgagaaa tgtgtatatg      1151
taatatataa ttgagtacta aaaaaaaaaa                                       1181
```

<210> SEQ ID NO 58
<211> LENGTH: 303
<212> TYPE: PRT
<213> ORGANISM: Lolium perenne

<400> SEQUENCE: 58

```
Met Ala Val Gln Gln Tyr Thr Val Ala Leu Phe Leu Ala Val Ala Ser
                -20                 -15                 -10

Cys Arg Ala Arg Ala Ser Tyr Ala Ala Asp Ala Gly Tyr Ala Pro Ala
            -5                  -1  1               5

Thr Pro Ala Thr Pro Ala Thr Pro Ala Ala Pro Gly Ala Ala Val Pro
        10                  15                  20

Ala Gly Lys Ala Ala Thr Glu Glu Gln Lys Leu Ile Glu Lys Ile Asn
25                  30                  35                  40

Ala Gly Phe Lys Ala Ala Val Ala Ala Ala Gly Val Pro Pro Gly
                45                  50                  55

Asp Lys Tyr Lys Thr Phe Val Glu Thr Phe Gly Lys Ala Ser Asn Lys
            60                  65                  70
```

-continued

```
Ala Phe Leu Gly Asp Leu Pro Thr Asn Tyr Ala Asp Val Asn Ser Arg
        75                  80                  85

Ala Gln Leu Thr Ser Lys Leu Asp Ala Ala Tyr Lys Leu Ala Tyr Asp
        90                  95                 100

Ala Ala Gln Gly Ala Thr Pro Glu Ala Lys Tyr Asp Ala Tyr Val Ala
105                 110                 115                 120

Thr Leu Ser Glu Ala Leu Arg Ile Ile Ala Gly Thr Leu Glu Val His
                125                 130                 135

Ala Val Lys Pro Ala Ala Glu Glu Val Lys Pro Ile Pro Ala Gly Glu
            140                 145                 150

Leu Gln Ile Val Asp Lys Ile Asp Val Ala Phe Arg Thr Ala Ala Thr
                155                 160                 165

Ala Ala Asn Ala Ala Pro Thr Asn Asp Lys Phe Thr Val Phe Glu Thr
            170                 175                 180

Thr Phe Asn Lys Ala Ile Lys Glu Ser Thr Gly Gly Thr Tyr Glu Ser
185                 190                 195                 200

Tyr Lys Phe Ile Pro Thr Leu Glu Ala Val Lys Gln Ala Tyr Ala
                205                 210                 215

Ala Thr Val Ala Ser Ala Pro Glu Lys Tyr Ala Val Phe Glu Thr
                220                 225                 230

Ala Leu Lys Lys Ala Val Thr Ala Met Ser Glu Ala Gln Lys Glu Ala
            235                 240                 245

Lys Pro Ala Thr Ala Thr Pro Thr Pro Thr Ala Thr Ala Ala Ala Ala
        250                 255                 260

Val Ala Thr Asn Ala Ala Pro Val Ala Ala Gly Gly Tyr Lys Ile
265                 270                 275

<210> SEQ ID NO 59
<211> LENGTH: 20
<212> TYPE: PRT
<213> ORGANISM: Lolium perenne

<400> SEQUENCE: 59

Ala Asp Ala Gly Tyr Thr Pro Ala Ala Ala Thr Pro Ala Thr Pro
  1               5                  10                  15

Ala Ala Thr Pro
            20

<210> SEQ ID NO 60
<211> LENGTH: 20
<212> TYPE: PRT
<213> ORGANISM: Lolium perenne

<400> SEQUENCE: 60

Ala Thr Pro Ala Thr Pro Ala Ala Thr Pro Ala Ala Ala Gly Gly Lys
  1               5                  10                  15

Ala Thr Thr Asp
            20

<210> SEQ ID NO 61
<211> LENGTH: 20
<212> TYPE: PRT
<213> ORGANISM: Lolium perenne

<400> SEQUENCE: 61

Ala Pro Tyr His Phe Asp Leu Ser Gly His Ala Phe Gly Ser Met Ala
  1               5                  10                  15

Lys Lys Gly Glu
```

```
<210> SEQ ID NO 62
<211> LENGTH: 20
<212> TYPE: PRT
<213> ORGANISM: Lolium perenne

<400> SEQUENCE: 62

Ala Phe Gly Ser Met Ala Lys Lys Gly Glu Glu Gln Lys Leu Arg Ser
1               5                   10                  15

Ala Gly Glu Leu
            20
```

T CELL EPITOPES OF RYEGRASS POLLEN ALLERGEN

RELATED APPLICATIONS

This application is the National Stage of PCT/US94/09024, filed Aug. 5, 1994 (published in English), which claims benefit of U.S. application Ser. No. 08/106,016, filed Aug. 13, 1993 now abandoned.

BACKGROUND OF THE INVENTION

Allergens constitute the most abundant proteins of grass pollen, which is the major cause of allergic disease in temperate climates (Marsh (1975) Allergens and the genetics of allergy; in M. Sela (ed.), The Antigens, Vol. 3, pp 271–359, Academic Press Inc., London, N.Y.)., Hill et al. (1979) Medical Journal of Australia, 1:426–429). The first descriptions of the allergenic proteins in ryegrass showed that they are immunochemically distinct, and are known as groups I, II, III and IV (Johnson and Marsh (1965) Nature, 206:935–942; and Johnson and Marsh (1966) Immunochemistry, 3:91–100). Using the International Union of Immunological Societies' (IUIS) nomenclature, these allergens are designated Lol p I, Lol p II, Lol p III and Lol p IV. In addition, another important Lolium perenne L. allergen that has been identified in the literature is Lol p IX which is also known as Lol p V or Lol p Ib (Singh et al. (1991) Proc. Natl. Acad. Sci, USA, 88:1384–1388).

These five proteins have been identified in pollen ryegrass, Lolium perenne L., and act as antigens in triggering immediate (Type 1) hypersensitivity in susceptible humans.

Lol p V is defined as an allergen because of its ability to bind to specific IgE in sera of ryegrass-sensitive patients, to act as an antigen in IgG responses and to trigger T-cell responses. The allergenic properties have been demonstrated by immunoblotting studies showing 80% of ryegrass pollen sensitive patients possessed specific IgE antibody that bound to Lol p V isoforms (PCT application publication number WO 93/04174, page 65). These results indicate that Lol p V is a major ryegrass allergen.

Substantial allergenic cross-reactivity between grass pollens has been demonstrated using an IgE-binding assay, the radioallergo-sorbent test (RAST), for example, as described by Marsh et al. (1970) J. Allergy, 46, 107–121, and Lowenstein (1978) Prog. Allergy, 25, 1–62. (Karger, Basel).

The immunochemical relationship of Lol p V with other grass pollen antigens have been demonstrated using both polyclonal and monoclonal antibodies (Zhang et al., Int. Arch Allergy Appl Immunol, 96:28–34 (1991); Roberts et al., Int. Arch Allergy Appl Immunol, 98:178–180 (1992); Mattheisen and Lowenstein, Clinical and Experimental Allergy, 21:309–320 (1991); and van Ree et al., J. Allergy Clin. Immunol. 83:144–151 (1989)). Antibodies have been prepared to purified proteins that bind IgE components. These data demonstrate that a major allergen is present in pollen of closely related grasses is immunochemically similar to Lol p V and are generally characterized as Group V allergens.

In view of the prevalence of ryegrass pollen allergens and related grass allergens all over the world, there is a pressing need for the development of compositions and methods that could be used in detecting sensitivities to Lol p V or other immunologically related grass allergens, or in treating sensitivities to such allergens, or in assisting in the manufacture of medicaments to treat such sensitivities. The present invention provides materials and methods having one or more of those utilities.

SUMMARY OF THE INVENTION

The present invention provides isolated peptides of Lol p V. Peptides within the scope of the invention comprise at least one T cell epitope, preferably at least two T cell epitopes of Lol p V. The invention further provides peptides comprising at least two regions, each region comprising at least one T cell epitope of Lol p V.

The invention also provides modified peptides having similar or enhanced therapeutic properties as the corresponding, naturally-occurring allergen or portion thereof, but having reduced side effects, as well as modified peptides having improved properties such as increased solubility and stability. Therapeutic peptides of the invention are capable of modifying, in a Lol p V-sensitive individual to whom they are administered, the allergic response of the individual to Lol p V or an allergen immunologically cross-reactive Lol p V e.g. allergens derived from pollen belonging to the Poacea (Graminae) family such as Dactylis glomerata, Dac g V.

Methods of treatment or of diagnosis of sensitivity to ryegrass pollen protein, Lol p V in an individual or to pollen proteins that are immunologically related to Lol p V such as Dac g V, and therapeutic compositions comprising one or more peptides of the invention are also provided.

The present invention also provides nucleic and amino acid sequences of Dac g V protein allergen which is immunologically cross-reative with Lol p V.

Further features of the present invention will be better understood from the following detailed description of the preferred embodiments of the invention in conjunction with the appended figures.

BRIEF DESCRIPTION OF THE FIGURES

FIG. 1A and FIG. 1B shows the nucleotide sequence of cDNA clone 12R (SEQ ID NO:1) and its predicted amino acid sequence (SEQ ID NO:2). Clone 12R is a full-length clone of Lol p V derived from a λgtII library (see PCT application publication number WO93/04174).

FIG. 2 shows peptides of the invention of various lengths derived from Lol p V (SEQ ID NO: 3–29, 60).

FIG. 3 shows peptides of various lengths derived from Lol p I (SEQ ID NO:30–53, 55, 56, 61, 62).

FIG. 13a and FIG. 13b each show a graphic representation of a direct ELISA using a sample of pooled human plasma designated PHP-B as a source of IgE, and wherein the antigen was either a selected peptide derived from Lol p V or rLol p V.

FIG. 16A, FIG. 16B, and FIG. 16C show the nucleotide sequence of clone 259 (SEQ ID NO:57) of Dac g V, and its predicted amino acid sequence (SEQ ID NO:58), the nucleotide sequence of nucleotides 1 to 699 has been confirmed, and the nucleotide sequence of nucleotides 700 to 1181 are unconfirmed.

DETAILED DESCRIPTION OF THE INVENTION

Figure 4:
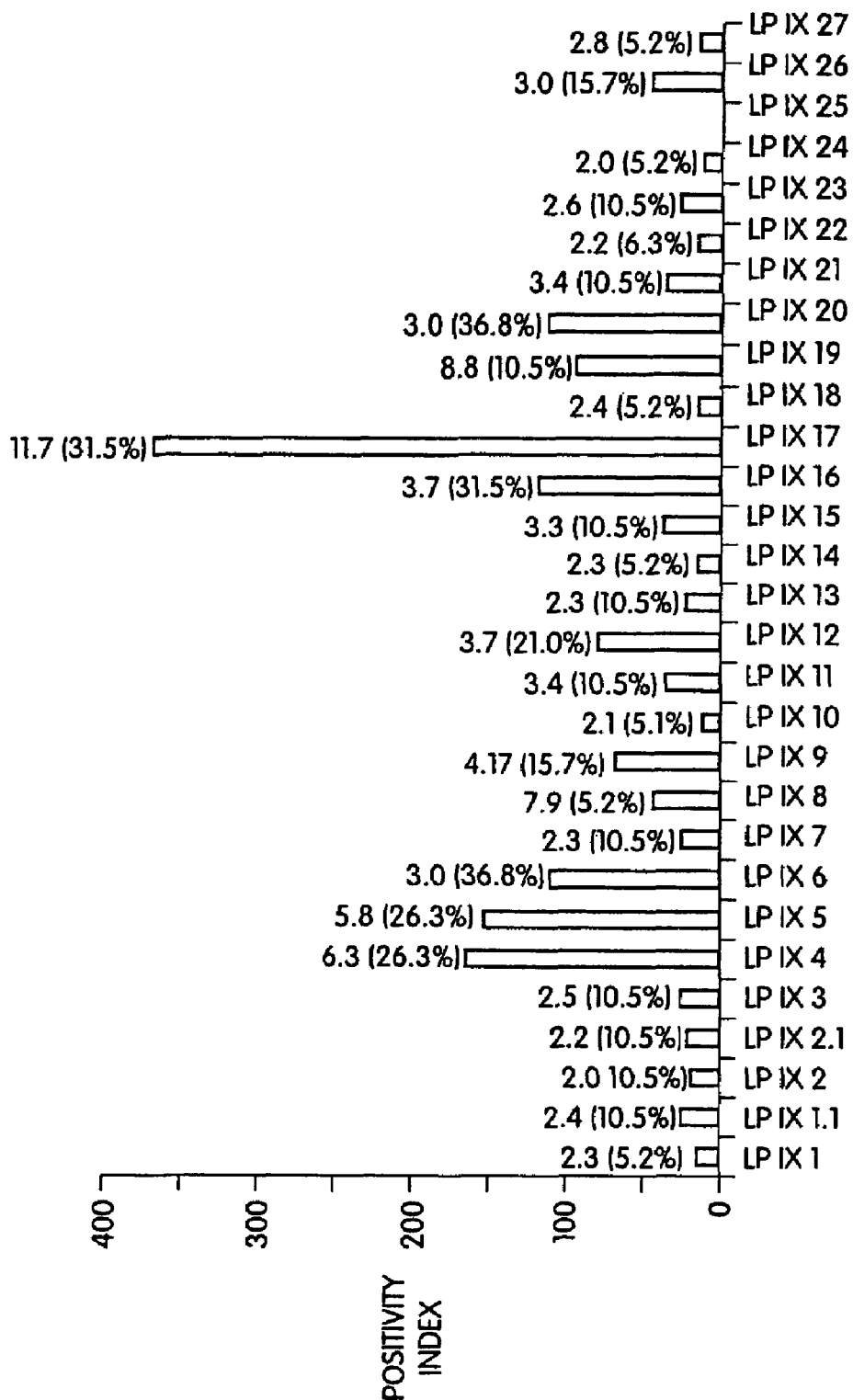
FIG. 4 is a graphic representation depicting the response of T cell lines from 19 patients primed in vitro with affinity purified Lol p V and analyzed for response to Lol p V peptides (derived from the Lol p V protein allergen) by percent of responses with a mean S.I. of at least 2 (indicated above each bar), the numbers enclosed in the parenthesis denote percentage of patients responding to the particular peptide, and the bar represents the positivity index for each peptide (% of patients responding multiplied by the mean S.I.).

The present invention provides isolated peptides derived from Lol p V. The present invention also provides Dac g V protein allergen which is immunologically cross-reactive with Lol p V. As used herein, a "peptide" refers to any protein fragment of Lol p V that induces an immune response. The terms "fragment" and "antigenic fragment" as used herein refer to an amino acid sequence having fewer amino acid residues than the entire amino acid sequence of the protein from which the fragment is derived, and that induces an immune response. The terms "isolated" and "purified" as used herein refer to peptides of the invention which are substantially free of cellular material or culture medium when produced by recombinant DNA techniques, or substantially free of chemical precursors or other chemicals when synthesized chemically. As used herein, the term "peptide" of the invention include peptides derived from Lol p V which comprise at least one T cell epitope of the allergen or a portion of such peptide which comprises at least one T cell epitope.

Peptides comprising at least two regions, each region comprising at least one T cell epitope of Lol p V are also within the scope of the invention. Isolated peptides or regions of isolated peptides, each comprising at least two T cell epitopes of Lol p V protein allergen are particularly desirable for increased therapeutic effectiveness. Peptides which are immunologically related (e.g., by antibody or T cell cross-reactivity) to peptides of the present invention, such as peptides from Dac g V, are also within the scope of the invention. Peptides immunologically related by antibody cross-reactivity, are bound by antibodies specific for a peptide of Lol p V. Peptides immunologically related by T cell cross-reactivity are capable of reacting with the same T cells as a peptide of the invention.

Isolated peptides of the invention can be produced by recombinant DNA techniques in a host cell transformed with a nucleic acid having a sequence encoding such peptide. The isolated peptides of the invention can also be produced by chemical synthesis. When a peptide is produced by recombinant techniques, host cells transformed with a nucleic acid having a sequence encoding a peptide of the invention or the functional equivalent of the nucleic acid sequence are cultured in a medium suitable for the cells and peptides can be purified from cell culture medium, host cells, or both using techniques known in the art for purifying peptides and proteins including ion-exchange chromatography, gel filtration chromatography, ultrafiltration, electrophoresis or immunopurification with antibodies specific for the peptide, the protein allergen from which the peptide is derived, or a portion thereof.

The present invention provides expression vectors and host cells transformed to express the nucleic acid sequences of the invention. Nucleic acid coding for a Lol p V peptide of the invention or at least one fragment thereof may be expressed in bacterial cells such as $E.\ coli$, insect cells, yeast, or mammalian cells such as Chinese hamster ovary cells (CHO). Suitable expression vectors, promoters, enhancers, and other expression control elements may be found in Sambrook et al. *Molecular Cloning: A Laboratory Manual*, second edition, Cold Spring Harbor Laboratory Press, Cold Spring Harbor, N.Y., 1989. Other suitable expression vectors, promoters, enhancers, and other expression elements are known to those skilled in the art. Suitable vectors for expression in yeast include YepSec1 (Baldari et al. (1987) *Embo J.* 6: 229–234); pMFa (Kurjan and Herskowitz (1982) *Cell* 30: 933–943); JRY88 (Schultz et al. (1987) *Gene* 54: 113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in $E.\ coli$, suitable expression vectors include, among others, pTRC (Amann et al. (1988) *Gene* 69: 301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.* 64:3963–3966; and pSEM (Knapp et al. (1990) *BioTechniques* 8: 280–281). The use of pTRC, and pET-11d, for example, will lead to the expression of unfused protein. The use of pMAL, pRIT5 pSEM and pGEX will lead to the expression of allergen fused to maltose E binding protein (pMAL), protein A (pRIT5), truncated β-galactosidase (PSEM), or glutathione S-transferase (pGEX). When a Lol p V peptide of the invention is expressed as a fusion protein, it is particularly advantageous to introduce an enzymatic cleavage site at the fusion junction between the carrier protein and Lol p V peptide. The Lol p V peptide may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant Lol p V peptides in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli*, where such nucleic acid alteration would not affect the amino acid sequence of the expressed protein.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be chemically synthesized using standard techniques (i.e. solid phase synthesis). Details of the isolation and cloning of clone 12R encoding Lol p V (described as Lol p Ib.1) are given in PCT application Publication Number WO 93/04174 incorporated herein by reference in its entirety.

Inducible non-fusion expression vectors include pTrc (Amann et al., (1988) *Gene*, 69:301–315) and pET11d (Studier et al., *Gene Expression Technology: Methods in Enzymology*, Academic Press, San Diego, Calif. (1990), 185:60–89). While target gene expression relies on host RNA polymerase transcription from the hybrid trp-lac fusion promoter in pTrc, expression of target genes inserted into pET11d relies on transcription from the T7 gn10-lac 0 fusion promoter mediated by coexpressed viral RNA polymerase (T7 gn1). This viral polymerase is supplied by host strains BL21 (DE3) or HMS174(DE3) from a resident λ prophage harboring a T7 gn1 under the transcriptional control of the lacUV 5 promoter.

One strategy to maximize recombinant Lol p V peptide expression in *E. coli* is to express the protein in a host bacteria with an impaired capacity to proteolytically cleave the recombinant protein (Gottesman, S., *Gene Expression Technology: Methods in Enzymology*, Academic Press, San Diego, Calif. (1990), 185:119–128). Another strategy would be to alter the nucleic acid sequence of the desired gene to be inserted into an expression vector so that the individual codons for each amino acid would be those preferentially utilized in highly expressed *E. coli* proteins (Wada et al. (1992) *Nuc. Acids Res*, 20:2111–2118). Such alteration of nucleic acid sequences of the invention could be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The present invention also provides nucleic acid sequences encoding peptides of the invention. Nucleic acid sequences used in any embodiment of this invention can be cDNAs encoding corresponding peptide sequences as shown in FIG. 2 (SEQ ID NO:3–29, 60). Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of Lol p V as shown in FIG. 1 or fragments thereof hybridizes, or 2) the sequence (the corresponding sequence portions complementary to the nucleic acid sequences encoding the peptide sequence derived from Lol p V as shown in FIGS. 2 and/or 3) a sequence which encodes a product (e.g., a polypeptide or peptide) having the same functional characteristics of the product encoded by the sequence (or corresponding sequence portion) of Lol p V as shown in FIG. 1. Whether a functional equivalent must meet one or more criteria will depend on its use (e.g., if it is to be used only as an oligoprobe, it need meet only the first or second criteria and if it is to be used to produce a Lol p V peptide of the invention, it need only meet the third criterion). The nucleic acid sequences of the invention also include RNA which can be transcribed from the DNA prepared as described above.

Preferred nucleic acids encode a peptide having at least about 50% homology to a Lol p V peptide of the invention, more preferably at least about 60% homology and most preferably at least about 70% homology with a Lol p V peptide of the invention. Nucleic acids that encode peptides having at least about 90%, more preferably at least about 95%, and most preferably at least about 98–99% homology with Lol p V peptides of the invention are also within the scope of the invention. Homology refers to sequence similarity between two peptides of Lol p V, or between two nucleic acid molecules. Homology can be determined by comparing a position in each sequence which may be aligned for purposes of comparison. When a position in the compared sequence is occupied by the same nucleotide or amino acid, then molecules are homologous at that position. A degree of homology between sequences is a function of the number of matching or homologous positions shared by the sequences.

Preferred nucleic acid fragments encode peptides of at least 7 amino acid residues in length, and preferably 13–40 amino acid residues in length, and more preferably at least 16–30 amino acids residues in length, Nucleic acid fragments encoding peptides of at least 30 amino acid residues in length, at least 40 amino acid residues in length, at least about 80 amino acid residues in length, at least about 100 amino acid residues in length or more, are also contemplated.

Also within the scope of the invention are nucleic acid sequences encoding allergens immunologically cross-reactive with Lol p V, such as full length Dac g V protein or peptides (FIG. 16). Proteins and peptides of Dac g V may be produced recombinantly as discussed above, or synthetically. Expression vectors and host cells transformed to express Dac g V protein or peptides thereof are also within the scope of the invention. Details of the cloning of Dac g V are given in the examples.

The present invention also provides a method of producing isolated Lol p V peptides of the invention or a portion thereof comprising the steps of culturing a host cell transformed with a nucleic acid sequence encoding a Lol p V peptide of the invention in an appropriate medium to produce a mixture of cells and medium containing said Lol p V peptide; and purifying the mixture to produce substantially pure Lol p V peptide. Host cells transformed with an expression vector containing DNA coding for a Lol p V peptide of the invention or a portion thereof are cultured in a suitable medium for the host cell. Lol p V peptides of the invention can be purified from cell culture medium, host cells, or both using techniques known in the art for purifying peptides and proteins including ion-exchange chromatography, gel filtration chromatography, ultrafiltration, electrophoresis and immunopurification with antibodies specific for the Lol p V peptides or portions thereof of the invention.

Another aspect of the present invention pertains to an antibody specifically reactive with a Lol p V peptide. Such antibodies may be used to standardize allergen extracts or to isolate the naturally occurring Lol p V. Also, Lol p V peptides of the invention can be used as "purified" allergens to standardize allergen extracts. For example, an animal such as a mouse or rabbit can be immunized with an immunogenic form of an isolated Lol p V peptide of the invention capable of eliciting an antibody response. Techniques for conferring immunogenicity on a peptide include conjugation to carriers or other techniques well-known in the art. The Lol p V peptide also can be administered in the presence of adjuvant. The progress of immunization can be monitored by detection of antibody titers in plasma or serum standard ELISA or other immunoassay can be used with the immunogen as antigen to assess the levels of antibodies.

Following immunization, anti-Lol p V peptide antisera can be obtained and, if desired, polyclonal anti-Lol p V peptide antibodies from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Hybridoma cells can be screened immunochemically for production of antibodies reactive with the Lol p V peptides of the invention. These sera or monoclonal antibodies can be used to standardize allergen extracts.

Through use of the peptides and antibodies of the present invention, preparations of consistent, well-defined composition and biological activity can be made and administered for therapeutic purposes (e.g. to modify the allergic response of a ryegrass pollen sensitive individual to pollen of such grasses or pollen of an immunologically related grass such as Dac g V). Administration of such peptides may, for example, modify B-cell response to Lol p V allergen, T-cell response to Lol p V allergen or both responses. Isolated peptides can also be used to study the mechanism of immunotherapy of ryegrass pollen allergy and to design modified derivatives or analogues useful in immunotherapy.

The present invention also pertains to T cell clones which specifically recognize Lol p V peptides of the invention. These T cell clones may be suitable for isolation and molecular cloning of the gene for the T cell receptor which is specifically reactive with a peptide of the present invention. The T cell clones may be produced as described in *Cellular and Molecular Immunology*, Abdul K. Abbas et al., W.B. Saunders Co. (1991) pg. 139. The present invention also pertains to soluble T cell receptors. These receptors may inhibit antigen-dependent activation of the relevant T cell subpopulation within an individual sensitive to Lol p V. Antibodies specifically reactive with such a T cell receptor can also be produced according to the techniques described herein. Such antibodies may also be useful to block T-cell-MHC interaction in an individual. Methods for producing soluble T cell receptors are described in *Immunology; A Synthesis*, 2nd Ed., Edward S. Golub et al., Sinaur Assoc, Sunderland Mass., (1991) pp. 366–369.

To obtain isolated peptides of the present invention, Lol p V is divided into non-overlapping peptides of desired length or overlapping peptides of desired lengths as discussed in Example 2 which can be produced recombinantly, synthetically, or in certain situations, by chemical cleavage of the allergen. Peptides comprising at least one T cell epitope are capable of eliciting a T cell response, such as stimulation (i.e. proliferation or lymphokine secretion) and/or are capable of inducing T cell non-responsiveness. To determine peptides comprising at least one T cell epitope, isolated peptides are tested by, for example, T cell biology techniques, to determine whether the peptides elicit a T cell response or induce T cell non-responsiveness. Those peptides found to elicit a T cell response or induce T cell non-responsiveness are defined as having T cell stimulating activity.

Screening peptides of the invention for human T cell stimulating acitivity can be accomplished using one or more of several different assays. For example, in vitro, T cell stimulatory activity is assayed by contacting a peptide of the invention with an antigen presenting cell which presents appropriate MHC molecules in a T cell culture. Presentation of a peptide of the invention in association with appropriate MHC molecules to T cells, in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86:1333 (1989) the pertinent portions of which are incorporated herein by reference. A kit for an assay for the production of interferon is also available from Genzyme Corporation (Cambridge, Mass.).

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

A peptide may also be screened for the ability to reduce T cell responsiveness. The ability of a peptide known to stimulate T cells, to inhibit or completely block the activity of a purified native Lol p V protein allergen or portion thereof and induce a state of T cell nonresponsiveness or reduced T cell responsiveness, can be determined using subsequent attempts at stimulation of the T cells with antigen presenting cells that present a native Lol p V allergen following exposure to a peptide of the invention. If the T cells are unresponsive to the subsequent activation attempts, as determined by interleukin-2 synthesis and T cell proliferation, a state of nonresponsiveness has been induced. See, e.g., Gimmi, et al. (1993) *Proc. Natl. Acad.* Sci USA, 90:6586–6590; and Schwartz (1990) *Science*, 248:1349–1356, for assay systems that can be used as the basis for an assay in accordance with the present invention.

Additionally, peptides comprising "cryptic epitopes" may be determined and are also within the scope of this invention. Cryptic epitopes are those determinants in a protein antigen which, due to processing and presentation of the native protein antigen to the appropriate MHC molecule, are not normally revealed to the immune system. However, a peptide comprising a cryptic epitope is capable of causing T cells to become non-responsive, and when a subject is primed with the peptide, T cells obtained from the subject will proliferate in vitro in response to the peptide or the protein antigen from which the peptide is derived. Peptides which comprise at least one cryptic epitope derived from a protein antigen are referred to herein as "cryptic peptides". To confirm the presence of cryptic epitopes in the above-described T cell proliferation assay, antigen-primed T cells are cultured in vitro in the presence of each peptide separately to establish peptide-reactive T cell lines. A peptide is considered to comprise at least one cryptic epitope if a T cell line can be established with a given peptide and T cells are capable of proliferation upon challenge with the peptide and the protein antigen from which the peptide is derived.

It is also possible to modify the structure of a peptide of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose.

For example, a peptide can be modified so that it maintains the ability to induce T cell anergy and bind MHC proteins without the ability to induce a strong proliferative response or possibly, any proliferative response when administered in immunogenic form. In this instance, critical binding residues for the T cell receptor can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate, or not affect T cell reactivity. In addition, those amino acid residues which are not essential for T cell receptor interaction can be modified by being replaced by another amino acid whose incorporation may enhance, diminish or not affect T cell reactivity but does not eliminate binding to relevant MHC.

Additionally, peptides of the invention can be modified by replacing an amino acid shown to be essential to interact with the MHC protein complex with another, preferably similar amino acid residue (conservative substitution) whose presence is shown to enhance, diminish but not eliminate, or not affect T cell activity. In addition, amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutamic acid, or a methyl amino acid.

In order to enhance stability and/or reactivity, peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified peptide within the scope of this invention. Furthermore, peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of peptides or portions thereof can also include reduction/alkylation (Tarr in: *Methods of Protein Microcharacterization*, J. E. Silver ed. Humana Press, Clifton, N.J., pp 155–194 (1986)); acylation (Tarr, supra); chemical coupling to an appropriate carrier (Mishell and Shiigi, eds., *Selected Methods in Cellular Immunology*, WH Freeman, San Francisco, Calif. (1980); U.S. Pat. No. 4,939,239; or mild formalin treatment (Marsh, *International Archives of Allergy and Applied Immunology*, 41:199–215 (1971)).

To facilitate purification and potentially increase solubility of peptides of the invention, it is possible to add reporter group(s) to the peptide backbone. For example, poly-histidine can be added to a peptide to purify the peptide on immobilized metal ion affinity chromatography (Hochuli, E. et al., *Bio/Technology*, 6:1321–1325 (1988)). In addition, specific endoprotease cleavage sites can be introduced, if desired, between a reporter group and amino acid sequences of a peptide to facilitate isolation of peptides free of irrelevant sequences. In order to successfully desensitize an individual to a protein antigen, it may be necessary to increase the solubility of a peptide by adding functional groups to the peptide or by not including hydrophobic T cell epitopes or regions containing hydrophobic epitopes in the peptides or hydrophobic regions of the protein or peptide. Functional groups such as charged amino acid pairs (e.g., KK or RR) are particularly useful for increasing the solubility of a peptide when added to the amino or carboxy terminus of the peptide.

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes. In addition, as discussed above, such charged amino acid residues can be added to the amino or carboxy terminus of the peptide and can result in an increase in solubility of a peptide.

Site-directed mutagenesis of DNA encoding a peptide of the invention can be used to modify the structure of the peptide by methods known in the art. Such methods may, among others, include PCR with oligonucleotides containing the sequences encoding the desired amino acids (Ho et al., *Gene*, 77:51–59 (1989)) or total synthesis of mutated genes (Hostomsky, Z. et al., *Biochem. Biophys, Res. Comm.*, 161:1056–1063 (1989)). To enhance bacterial expression, the aforementioned methods can be used in conjunction with other procedures to change the eukaryotic codons in DNA constructs encoding protein or peptides of the invention to ones preferentially used in *E. coli*, yeast, mammalian cells, or other eukaryotic cells.

Peptides or antibodies of the present invention can also be used for detecting and diagnosing ryegrass pollinosis. For example, this could be done in vitro by combining blood or blood products obtained from an individual to be assessed for sensitivity to ryegrass pollen or another cross reactive pollen such as Dac g V, with isolated peptides of Lol p V, under conditions appropriate for binding of components in the blood (e.g., antibodies, T cells, B cells) with the peptide(s) and determining the extent to which such binding occurs. Other diagnostic methods for allergic diseases in which the protein, peptides or antibodies of the present invention will be useful include radio-allergergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The presence in individuals of IgE specific for at least one protein allergen and the ability of T cells of the individuals to respond to T cell epitope(s) of the protein allergen can be determined by administering to the individuals an Immediate Type Hypersensitivity test and a Delayed Type Hypersensitiity test. The individuals are administered an Immediate Type Hypersensitivity test (see e.g., *Immunology* (1985) Roitt, I. M., Brostoff, J., Male, D. K. (eds), C.V. Mosby Co., Gower Medical Publishing, London, N.Y., pp. 19.2–19.18; pp. 22.1–22.10) utilizing the protein allergen or a portion thereof, or a modified form of the protein allergen or a portion thereof, each of which binds IgE specific for the allergen. The same individuals are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those individuals exhibiting a specific Immediate Type Hypersensitivity reaction. The Delayed Type Hypersensitivity test utilizes a modified form of the protein allergen or a portion thereof, the protein allergen produced recombinantly, or a peptide derived from the protein allergen, each of which has human T cell stimulating activity and each of which does not bind IgE specific for the allergen in a substantial percentage of the population of individuals sensitive to the allergen (e.g., at least about 75%). Those individuals found to have both a specific Immediate Type Hypersensitivity reaction and a specific Delayed Type Hypersensitivity reaction may be treated with a therapeutic composition comprising the same modified form of the protein or portion thereof, the recombinantly produced protein allergen, or the peptide, each as used in the Delayed Type Hypersensitivity test.

Isolated peptides of the invention when administered in a therapeutic regimen to a Lol p V-sensitive individual, or an individual allergic to an allergen cross-reactive with Lol p V such as Dac g V, are capable of modifying the allergic response of the individual to Lol p V ryegrass pollen allergen or such cross-reactive allergen, and preferably are capable of modifying the B-cell response, T-cell response or both the B-cell and the T-cell response of the individual to the allergen. As used herein, modification of the allergic response of an individual sensitive to a ryegrass pollen allergen or cross-reactive allergen can be defined as non-responsiveness or diminution in symptoms to the allergen, as determined by standard clinical procedures (See e.g. Varney et al, *British Medical Journal*, 302:265–269 (1990)) including diminution in ryegrass pollen induced asthmatic symptoms. As referred to herein, a diminution in symptoms includes any reduction in the allergic response of an individual to the allergen after the individual has completed a treatment regimen with a peptide or protein of the invention. This diminution may be subjective (i.e. the patient feels more comfortable in the presence of the allergen). Diminution in symptoms can be determined clinically as well, using standard skin tests as is known in the art.

Lol p V peptides of the present invention which have T cell stimulating activity, and thus comprise at least one T cell epitope are particularly desirable for therapeutic purposes. In referring to an epitope, the epitope will be the basic element or smallest unit of recognition by a receptor, particularly immunoglobulins, histocompatibility antigens and T cell receptors where the epitope comprises amino acids essential to receptor recognition. Amino acid sequences which mimic those of the epitopes and which are capable of down regulating or reducing allergic response to Lol p V can also be used. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted.

Exposure of ryegrass pollen patients to isolated Lol p V peptides of the present invention which comprise at least one T cell epitope and are derived from Lol p V protein allergen may cause appropriate T cell subpopulations to become nonresponsive or have a reduced response to the protein allergen and thus do not participate in stimulating an immune response upon such exposure. In addition, administration of a peptide of the invention or portion thereof which comprises at least one T cell epitope may modify the lymphokine secretion profile as compared with exposure to the naturally-occurring Lol p V protein allergen or portion thereof (e.g. result in a decrease of IL-4 and/or an increase in IL-2). Furthermore, administration of such peptide of the invention may influence T cell subpopulations which normally participate in the response to the naturally occurring allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a diminution in allergic symptoms.

The isolated Lol p V peptides of the invention can be used in methods of diagnosing, treating and preventing allergic reactions to Lol p V allergen or a cross reactive protein allergen. Thus the present invention provides compositions useful in allergy diagnosis and/or useful in allergy therapy comprising isolated Lol p V peptides or portions thereof. Such compositions will typically also comprise a pharmaceutically acceptable carrier or diluent when intended for in vivo administration. Therapeutic compositions of the invention may also comprise synthetically prepared Lol p V peptides and a pharmaceutically acceptable carrier or diluent.

Administration of the therapeutic compositions of the present invention to an individual to be desensitized can be carried out using known techniques. Lol p V peptides or portions thereof may be administered to an individual in combination with, for example, an appropriate diluent, a carrier and/or an adjuvant. Pharmaceutically acceptable diluents include saline and aqueous buffer solutions. Pharmaceutically acceptable carriers include polyethylene glycol (Wie et al. (1981) *Int. Arch Allergy Appl. Immunol.* 64:84–99) and liposomes (Strejan et al. (1984) *J. Neuroimmunol,* 7: 27).

The therapeutic compositions of the invention are administered to ryegrass allergen sensitive individuals or individuals sensitive to an allergen which is immunologically cross-reactive with house ryegrass allergen (i.e. *Dactylis glomerata,* or *Sorghum halepensis,* etc.). For:

the purposes of inducing T cell non responsiveness, therapeutic compositions of the invention are preferably administered in non-immunogenic form, e.g. which does not contain adjuvant. While not intending to be limited to any theory, it is believed that T cell non responsiveness or reduced T cell responsiveness is induced as a result of not providing an appropriate costimulatory signal sometimes referred to as a "second signal" Briefly, it is believed that stimulation of T cells requires two types of signals, the first is the recognition by the T cell via the T cell receptor of appropriate MHC-associated processed antigens on antigen presenting cells (APCs) and the second type of signal is referred to as a costimulatory signal(s) or "second signal" which may be provided by certain competent APCs. When a composition of the invention is administered without adjuvant, it is believed that competent APCs which are capable of producing the second signal or costimulatory signal are not engaged in the stimulation of appropriate T cells therefore resulting in T cell nonresponsiveness or reduced T cell responsiveness. In addition, there are a number of antibodies or other reagents capable of blocking the delivery of costimulatory signals such as the "second signal" which include, but are not limited to B7 (including B7-1, B7-2, and BB-1), CD28, CTLA4, CD40 CD40L CD54 and CD11a/18 (Jenkins and Johnson, *Current Opinion in Immunology,* 5:361–367 (1993), and Clark and Ledbetter, *Nature,* 367:425–428 (1994)) Thus, a peptide of the invention may be administered in nonimmunogenic form as discussed above, in conjunction with a reagent capable of blocking costimulatory signals such that the level of T cell nonresponsiveness is enhanced.

Administration of the therapeutic compositions of the present invention to an individual to be desensitized can be carried out using known procedures at dosages and for periods of time effective to reduce sensitivity (i.e., reduce the allergic response) of the individual to the allergen. Effective amounts of the therapeutic compositions will vary according to factors such as the degree of sensitivity of the individual to ryegrass pollen, the age, sex, and weight of the individual, and the ability of the protein or fragment thereof to elicit an antigenic response in the individual.

The active compound (i.e., protein or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound.

For example, preferably about 1 µg–3 mg and more preferably from about 20–750 µg of active compound (i.e., protein or fragment thereof) per dosage unit may be administered by injection. Dosage regimen may be adjusted to provide the optimum therapeutic response. For example, several divided doses may be administered daily or the dose may be proportionally reduced or increased as indicated by the exigencies of the therapeutic situation.

To administer a peptide by other than parenteral administration, it may be necessary to coat the protein with, or co-administer the protein with, a material to prevent its inactivation. For example, peptide or portion thereof may be co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.,* 7:27).

The active compound may also be administered parenterally or intraperitoneally. Dispersions can also be prepared in glycerol, liquid polyethyline glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions of dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glyceral, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thirmerosal, and the like. In many cases, it will be preferable to include isotonic agents, for example, sugars, polyalcohols such as manitol and sorbitol or sodium chloride in the composition. Prolonged absorption of the injectable compositions can be brought about, including in the composition, an agent which delays absorption, for example, aluminum monostearate and gelatin.

Sterile injectable solutions can be prepared by incorporating active compound (i.e., protein or peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile indectable solutions, the preferred methods of preparation are vacuum drying and freeze-drying which yields a powder of the active ingredient (i.e., protein or peptide) plus any additional desired ingredient from a previously sterile-filtered solution thereof.

When a peptide of the invention is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained. Preferred compositions or preparations according to the present invention are prepared so that an oral dosage unit contains between from about 10 µg to about 200 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplate Supplementary active compounds can also be incorporated into the compositions.

It is especially advantageous to formulate parenteral compositions in dosage unit form for ease of administration and uniformity of dosage. Dosage unit from as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the novel dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Various isolated peptides of the invention derived from ryegrass pollen protein Lol p V are shown in FIG. 2 (SEQ ID NO:3–29, 60). Peptides comprising at least two regions, each region comprising at least one T cell epitope of Lol p V are also within the scope of the invention. As used herein a region may include the amino acid sequence of a peptide of the invention as shown in FIG. 2 or the amino acid sequence of a portion of such peptide.

Figure 5:
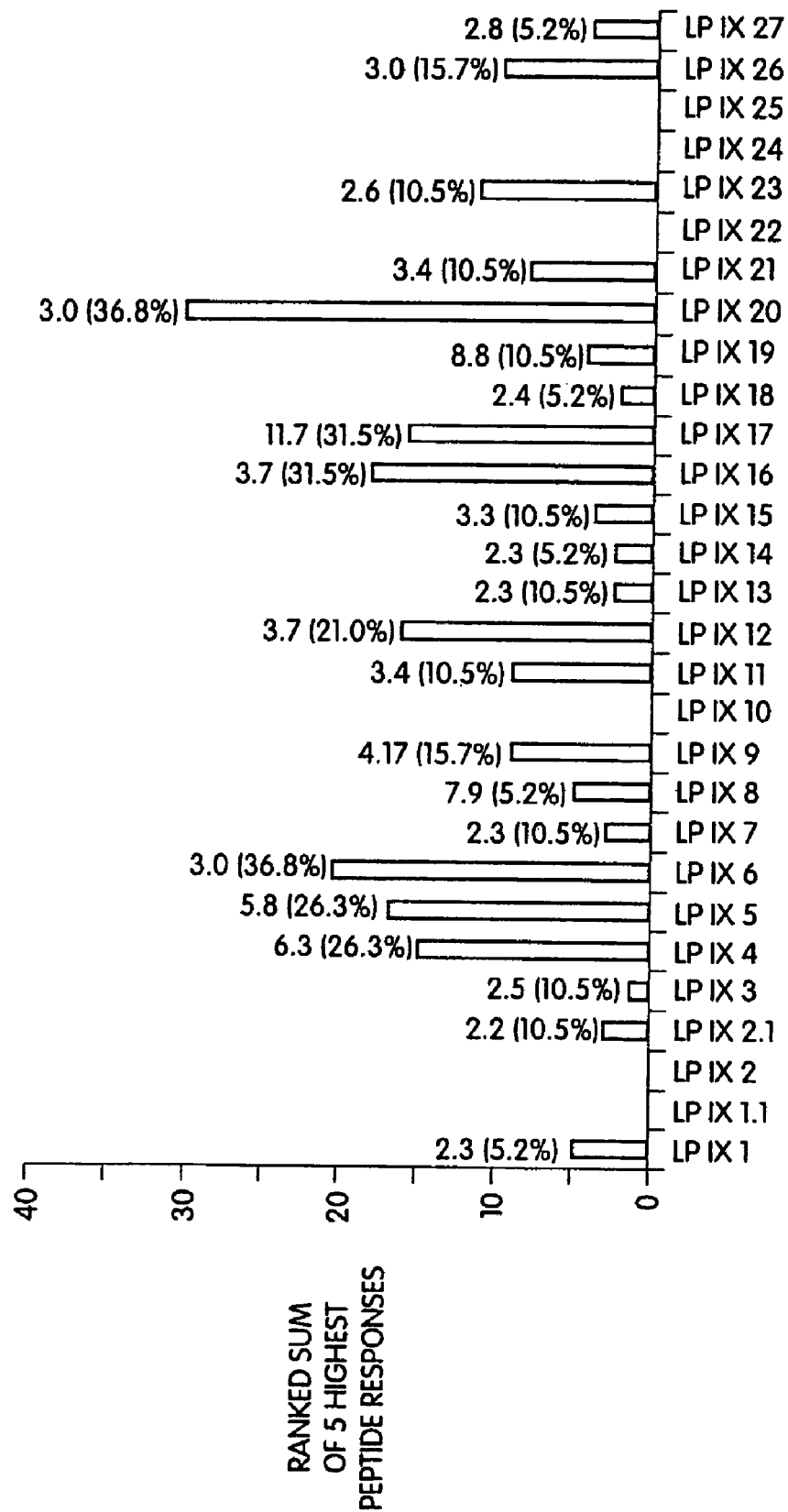
FIG. 5 is a graphic representation derived from the same data shown in FIG. 4 showing the ranked sum for each peptide, the bar represents the cumulative rank of the peptide response in the group of 19 patients tested, above each bar in parenthesis is the percent of patients positively responding to each peptide, the S.I. is also indicated above each bar.

As discussed in Example 2, human T cell stimulating activity can be tested by culturing T cells obtained from an individual sensitive to Lol p V allergen, (i.e., an individual who has an IgE mediated immune response to Lol p V allergen) with a peptide derived from the allergen and determining whether proliferation of T cells occurs in response to the peptide as measured, e.g., by cellular uptake of tritiated thymidine. Stimulation indices for responses by T cells to peptides can be calculated as the maximum CPM in response to a peptide divided by the control CPM. A stimulation index (S.I.) equal to or greater than two times the background level is considered "positive". Positive results are used to calculate the mean stimulation index for each peptide for the group of patients tested. In FIGS. 4 and 5 the mean T cell stimulation index is indicated above the bar. Preferred peptides of this invention comprise at least one T cell epitope and have a mean T cell stimulation index of greater than or equal to 2.0. A peptide having a mean T cell stimulation index of greater than or equal to 2.0 in a significant number of ryegrass pollen sensitive patients tested is considered useful as a therapeutic agent. Preferred peptides have a mean T cell stimulation index of at least 2.5, more preferably at least 3.0, more preferably at least 3.5, more preferably at least 4.0, more preferably at least 5.0 and most preferably at least about 6. For example, peptides of the invention having a mean T cell stimulation index of at least 5, as indicated by data shown in FIGS. 4 and 5, include peptides LPIX-4 (SEQ ID NO:6), LPIX-5 (SEQ ID NO:7), LPIX-8 (SEQ ID NO:10), LPIX-17 (SEQ ID NO:19) and LPIX-19 (SEQ ID NO:21).

In addition, preferred peptides have a positivity index (P.I.) of at least about 60, more preferably about 100, more preferably at least about 200 and most preferably at least about 300. The positivity index for a peptide is determined by multiplying the mean T cell stimulation index by the percent of individuals, in a population of individuals sensitive to ryegrass pollen (e.g., preferably a population of at least 15 individuals, more preferably a population of at least 30 individuals or more), who have a T cell stimulation index to such peptide of at least 2.0. Thus, the positivity index represents both the strength of a T cell response to a peptide (S.I.) and the frequency of a T cell response to a peptide in a population of individuals sensitive to ryegrass pollen. In FIG. 4, the bar represents the positivity index and the percent of individuals tested who have a T cell stimulation index of at least 2.0 to that peptide are indicated in parenthesis above each bar (the mean T cell stimulation index is also indicated above each bar). For example, as shown in FIG. 4, Lol p V peptide LPIX-5 (SEQ ID NO:7) has a mean S.I. of 5.8 and 26.3% of positive responses in the group of individuals tested resulting in a positivity index of 152.54. Lol p V peptides having a positivity index of at least about 100 and a mean T cell stimulation index of at least about 4 include: LPIX-4 (SEQ ID NO:6), LPIX-5 (SEQ ID NO:7), and LPIX-17 (SEQ ID NO:19).

In FIG. 5, the bar represents the cumulative rank of the peptide response in the group of patients tested as described in Example 2. To determine the cumulative rank, the 5 peptides with the highest S.I. in each individual were determined and assigned a numerical rank in descending order, with 5 representing the strongest response. The ranks for each peptide were then summed for the entire group of patients tested to determine the cumulative rank for the peptide. Above each bar is the mean S.I. for each peptide and the percent of positive responses (in parenthesis) with an S.I. of at least 2 to the peptide in the group of patients tested.

In order to determine precise T cell epitopes by, for example, fine mapping techniques, a peptide having T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. Following this technique, peptides are selected and produced recombinantly or synthetically. Peptides are selected based on various factors, including the strength of the T cell response to the peptide (e.g., stimulation index), the frequency of the T cell response to the peptide in a population of individuals sensitive to ryegrass pollen, and the potential cross-reactivity of the peptide with other allergens from other species of grasses as discussed earlier i.e. *Dactylis glomerata*. The physical and chemical properties of these selected peptides (e.g., solubility, stability) are examined to determine whether the peptides are suitable for use in therapeutic compositions or whether the peptides require modification as described herein. The ability of the selected peptides or selected modified peptides to stimulate human T cells (e.g., induce proliferation, lymphokine secretion) or cause appropriate T cell populations to become non-responsive or have a reduced response to the protein allergen is determined.

In addition, it may be desirable to further modify peptides such as LPIX-4 (SEQ ID NO:6), -5 (SEQ ID NO:7), -6 (SEQ ID NO:8), -11 (SEQ ID NO:13), -12 (SEQ ID NO:14), -16 (SEQ ID NO:18), -17 (SEQ ID NO:19) and -20 (SEQ ID NO:22) for purposes of increasing solubility or stability. Modifications to improve solubility include truncation from either the amino or carboxyl terminus of the peptide or both termini to remove hydrophilic amino acids such as Val, Ile, Leu, Phe, Tyr and Trp. Residues removed by truncation may also be replaced with charged hydrophilic amino acids such as Asp, Glu, Lys and Arg or neutral hydrophilic amino acids such as Ser, Pro, Gly or Ala. Such amino acids may be of either the R or S optical configuration.

Other modifications to improve solubility include attachment of hydrophilic polymers to either the amino- or carboxy terminus of the peptides or to both. Such polymers may be polyanionic, polycationic or neutral (such as polyoxyethylene).

Modifications to improve stability include deletion or replacement of Asn and Gln residues and elimination of Asn-Gly, Asp-Gly and Asp-Pro sequences.

Specific examples of modifications listed above would be removal of the N-terminal Val and C-terminal Val-His-Ala-Val from peptide LIX-12. The resulting truncated peptide could be used directly or the deleted residues could be replaced by combinations of the polar amino acids Asp, Glu, Lys and Arg. Similarly, the N-terminal sequence Gly-Phe and C-terminal sequence Phe-Lys-Ile could be removed from peptide LPIX-5 (SEQ ID NO:7).

Additionally, preferred T cell epitope-containing peptides of the invention do not bind immunoglobulin E (IgE) or bind IgE to a substantially lesser extent (e.g. at least 100 fold less and more preferably at least 1000 fold less) than the protein allergen from which the peptide is derived. The major complications of standard immunotherapy are IgE-mediated responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotacic factors). Thus, anaphylaxis in a substantial percentage of a population of individuals sensitive to Lol p V could be avoided by the use in immunotherapy of a peptide or peptides which do not bind IgE in a substantial percentage (e.g., at least about 75%) of a population of individuals sensitive to Lol p V allergen, or if the peptide binds IgE, such binding does not result in the release of mediators from mast cells or basophils. The risk of anaphylaxis could be reduced by the use in immunotherapy of a peptide or peptides which have reduced IgE binding. Moreover, peptides which have minimal IgE stimulating activity are desirable for therapeutic effectiveness. Minimal IgE stimulating activity refers to IgE production that is less than the amount of IgE production and/or IL-4 production stimulated by the native Lol p V protein allergen. Similarly, IL-4 production can be compared, with reduced IL-4 production indicating lessened IgE stimulating activity.

If a peptide of the invention is to be used as a diagnostic reagent, it is not necessary that the peptide or protein have reduced IgE binding activity compared to the native Lol p V allergen. IgE binding activity of peptides can be determined by, for example, using various types of enzyme linked immunosorbent assays (ELISA).

Preferred T cell epitope containing peptide of the invention, when administered to a ryegrass pollen-sensitive individual or an individual sensitive to an allergen which is immunologically related to ryegrass pollen allergen such as Dac g I, in a therapeutic treatment regimen, is capable of modifying the allergic response of the individual to the allergen. Particularly, such preferred Lol p V peptides of the invention comprising at least one T cell epitope of Lol p V or at least two regions derived from Lol p V, each comprising at least one T cell epitope, when administered to an individual sensitive to ryegrass pollen are capable of modifying T cell response of the individual to the allergen and are useful as therapeutics in addressing sensitivity to grasses.

A preferred isolated Lol p V peptide of the invention comprises at least one T cell epitope of the Lol p V and accordingly the peptide comprises at least approximately seven amino acid residues. For purposes of therapeutic effectiveness, preferred therapeutic compositions of the invention preferably comprise at least two T cell epitopes of Lol p V, and accordingly, a preferred peptide comprises at least approximately eight amino acid residues and preferably at least fifteen amino acid residues. Additionally, therapeutic compositions comprising preferred isolated peptides of the invention preferably comprise a sufficient percentage of the T cell epitopes of the entire protein allergen (i.e. at least about 40% and more preferably about 60% of the T cell reactivity to the entire protein allergen) such that a therapeutic regimen of administration of the composition to an individual sensitive to ryegrass pollen, results in T cells of the individual being tolerized to the protein allergen. Synthetically produced peptides of the invention comprising up to approximately forty-five amino acid residues in length, and most preferably up to approximately thirty amino acid residues in length are particularly desirable as increases in length may result in difficulty in peptide synthesis. Peptides of the invention may also be produced recombinantly as described earlier, and it is preferable that peptides of 45 amino acids or longer be produced recombinantly.

Peptides derived from the Lol p V protein allergen which can be used for therapeutic purposes comprise at least one T cell epitope of Lol p V and comprise all or a portion of the following peptides: LPIX-1 (SEQ ID NO:3), LPIX-1.1 (SEQ ID NO:59), LPIX-2 (SEQ ID NO:4), LPIX-2.1 (SEQ ID NO:60), LPIX-3 (SEQ ID NO:5), LPIX-4 (SEQ ID NO:6), LPIX-5 (SEQ ID NO:7), LPIX-6 (SEQ ID NO:8), LPIX-7 (SEQ ID NO:9), LPIX-8 (SEQ ID NO:10), LPIX-9 (SEQ ID NO:11), LPIX-10 (SEQ ID NO:12), LPIX-11 (SEQ ID NO:13), LPIX-12 (SEQ ID NO:14), LPIX-13 (SEQ ID NO:15), LPIX-14 (SEQ ID NO:16), LPIX-15 (SEQ ID NO:17), LPIX-16 (SEQ ID NO:18), LPIX-17 (SEQ ID NO:19), LPIX-18 (SEQ ID NO:20), LPIX-19 (SEQ ID NO:21), LPIX-20 (SEQ ID NO:22), LPIX-21 (SEQ ID NO:23), LPIX-22 (SEQ ID NO:24), LPIX-23

(SEQ ID NO:25), LPIX-24 (SEQ ID NO:26), LPIX-26 (SEQ ID NO:28), and LPIX-27 (SEQ ID NO:29) (the sequences of which are shown in FIG. 2) wherein the portion of the peptide preferably has a mean T cell stimulation index (S.I.) equivalent to, or greater than the mean T cell stimulation index of the peptide from which it is derived (e.g. as shown in FIG. 5, the S.I. for LPIX-16 (SEQ ID NO:18) is shown above the bar to be 3.7, therefore any portion of LPIX-16 preferably has a mean S.I. of 3.7). Even more preferably peptides derived from the Lol p V protein allergen which can be used for therapeutic purposes comprise all or a portion of the following peptides: LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25), and LPIX-26 (SEQ ID NO:28) as shown in FIG. 2. Even more preferably, peptides derived from Lol p V protein allergen which can be used for therapeutic purposes comprise all or a portion of the following peptides: LPIX-1 (SEQ ID NO:3), LPIX-2 (SEQ ID NO:4), LPIX-3 (SEQ ID NO:5), LPIX-4 (SEQ ID NO:6), LPIX-5 (SEQ ID NO:7), LPIX-6 (SEQ ID NO:8), LPIX-7 (SEQ ID NO:9), LPIX-8 (SEQ ID NO:10), LPIX-9 (SEQ ID NO:11), LPIX-10 (SEQ ID NO:12), LPIX-11 (SEQ ID NO:13), LPIX-12 (SEQ ID NO:14), LPIX-13 (SEQ ID NO:15), LPIX-14 (SEQ ID NO:16), LPIX-15 (SEQ ID NO:17), LPIX-16 (SEQ ID NO:18), LPIX-17 (SEQ ID NO:19), LPIX-18 (SEQ ID NO:20), LPIX-19 (SEQ ID NO:21), LPIX-20 (SEQ ID NO:22), LPIX-21 (SEQ ID NO:23), LPIX-22 (SEQ ID NO:24), LPIX-23 (SEQ ID NO:25), LPIX-24 (SEQ ID NO:26), LPIX-26 (SEQ ID NO:28), and LPIX-27 (SEQ ID NO:29).

One embodiment of the present invention features a peptide or portion thereof of Lol p V which comprises at least one T cell epitope of the protein allergen and has a formula $X_n$-Y-$Z_m$. According to the formula, Y is an amino acid sequence selected from the group consisting of LPIX-1 (SEQ ID NO: 3), LPIX-1.1 (SEQ ID NO:59), LPIX-2 (SEQ ID NO: 4), LPIX-2.1 (SEQ ID NO:60), LPIX-3 (SEQ ID NO: 5), LPIX-4 (SEQ ID NO: 6), LPIX-5 (SEQ ID NO: 7), LPIX-6 (SEQ ID NO: 8), LPIX-7 (SEQ ID NO: 9), LPIX-8 (SEQ ID NO: 10), LPIX-9 (SEQ ID NO: 11), LPIX-10 (SEQ ID NO: 12), LPIX-11 (SEQ ID NO: 13), LPIX-12 (SEQ ID NO: 14), LPIX-13 (SEQ ID NO: 15), LPIX-14 (SEQ ID NO: 16), LPIX-15 (SEQ ID NO: 17), LPIX-16 (SEQ ID NO: 18), LPIX-17 (SEQ ID NO: 19), LPIX-18 (SEQ ID NO: 20), LPIX-19 (SEQ ID NO: 21), LPIX-20 (SEQ ID NO: 22), LPIX-21 (SEQ ID NO: 23), LPIX-22 (SEQ ID NO: 24), LPIX-23 (SEQ ID NO: 25), LPIX-24 (SEQ ID NO: 26), LPIX-26 (SEQ ID NO: 28), and LPIX-27 (SEQ ID NO: 29) (the sequences of which are shown in FIG. 2). In addition, $X_n$ are amino acid residues contiguous to the amino terminus of Y in the amino acid sequence of the protein allergen and $Z_m$ are amino acid residues contiguous to the carboxy terminus of Y in the amino acid sequence of the protein allergen. In the formula, n is 0–30 and m is 0–30. Preferably, the peptide or portion thereof has a mean T cell stimulation index equivalent to greater than the mean T cell stimulation index of Y as shown in FIG. 4. Preferably, amino acids comprising the amino terminus of X and the carboxy terminus of Z are selected from charged amino acids, i.e., arginine (R), lysine (K), histidine (H), glutamic acid (E) or aspartic acid (D); amino acids with reactive side chains, e.g., cysteine (C), asparagine (N) or glutamine (Q); or amino acids with sterically small side chains, e.g., alanine (A) or glycine (G). Preferably n and m are 0–5; most preferably n+m is less than 10.

Another embodiment of the present invention provides peptides comprising at least two regions, each region comprising at least one T cell epitope of Lol p V and accordingly each region comprises at least approximately seven amino acid residues. These peptides comprising at least two regions can comprise up to 100 or more amino acid residues but preferably comprise at least about 14, even more preferably at least about 20, and most preferably at least about 30 amino acid residues of the Lol p V allergen. If desired, the amino acid sequences of the regions can be produced and joined by a linker to increase sensitivity to processing by antigen-presenting cells. Such linker can be any non-epitope amino acid sequence or other appropriate linking or joining agent. To obtain preferred peptides comprising at least two regions, each comprising at least one T cell epitope, the regions are arranged in the same or a different configuration from a naturally-occurring configuration of the regions in the allergen. For example, the regions containing T cell epitope(s) can be arranged in a noncontiguous configuration and can preferably be derived from the same protein allergen. Noncontiguous is defined as an arrangement of regions containing T cell epitope(s) which is different than that of the native amino acid sequence of the protein allergen from which the regions are derived. Furthermore, the noncontiguous regions containing T cell epitopes can be arranged in a nonsequential order (e.g., in an order different from the order of the amino acids of the native protein allergen from which the region containing T cell epitope(s) are derived in which amino acids are arranged from an amino terminus to a carboxy terminus). A peptide of the invention can comprise at least 15%, at least 30%, at least 50% or up to 100% of the T cell epitopes of Lol p V but does not comprise the entire amino acid sequence of Lol p V.

The individual peptide regions can be produced and tested to determine which regions bind immunoglobulin E specific for Lol p V and which of such regions would cause the release of mediators (e.g., histamine) from mast cells or basophils. Those peptide regions found to bind immunoglobulin E and to cause the release of mediators from mast cells or basophils in greater than approximately 10–15% of the allergic sera tested are preferably not included in the peptide regions arranged to form preferred peptides of the invention.

Examples of preferred peptide regions which do not appear to bind to IgE in preliminary IgE binding data studies (Example 3) include the amino acid sequences of such regions being shown in FIG. 2 (SEQ ID NO:3–29), or portions of said regions comprising at least one T cell epitope.

Preferred peptides comprise various combinations of two or more of the above-discussed preferred regions, or a portion thereof. Preferred peptides comprising a combination of two or more regions (each region having an amino acid sequence as shown in FIG. 2), include the following:

LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), and LPIX-20 (SEQ ID NO:22);

LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), and LPIX-20 (SEQ ID NO:22);

LPIX-4 (SEQ ID NO:6), LPIX-5 (SEQ ID NO:7), LPIX-6 (SEQ ID NO: 8), LPIX-17 (SEQ ID NO:19) and LPIX-20 (SEQ ID NO:22);

LPIX-4 (SEQ ID NO:6), LPIX-5 (SEQ ID NO:7), LPIX-6 (SEQ ID NO:8) and LPIX-20 (SEQ ID NO:22);

LPIX-4 (SEQ ID NO:6), LPIX-5 (SEQ ID NO:7), LPIX-6 (SEQ ID NO:8), LPIX-11 (SEQ ID NO:13), LPIX-12 (SEQ ID NO:14), LPIX-16 (SEQ ID NO:18), LPIX-17 (SEQ ID NO:19) and LPIX-20 (SEQ ID NO:22);

LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25) and LPIX-26 (SEQ ID NO:28);

LPIX-4 (SEQ ID NO:6), LPIX-1 I (SEQ ID NO: 13), LPIX-16 (SEQ ID NO:18), and LPIX-20 (SEQ ID NO:22);

LPIX-4 (SEQ ID NO:6), LPIX-11 (SEQ ID NO: 13), LPIX-17 (SEQ ID NO:19), and LPIX-20 (SEQ ID NO:22);

LPIX-4 (SEQ ID NO:6), LPIX-16 (SEQ ID NO:18), LPIX-17 (SEQ ID NO:19), and LPIX-20 (SEQ ID NO:22);

LPIX-5 (SEQ ID NO:7), LPIX-11 (SEQ ID NO: 13), LPIX-16 (SEQ ID NO:18), and LPIX-20 (SEQ ID NO:22);

LPIX-5 (SEQ ID NO:7), LPIX-11 (SEQ ID NO: 13), LPIX-17 (SEQ ID NO:19), and LPIX-20 (SEQ ID NO:22);

LPIX-5 (SEQ ID NO:7), LPIX-16 (SEQ ID NO:18), LPIX-17 (SEQ ID NO:19), and LPIX-20 (SEQ ID NO:22);

LPIX-11 (SEQ ID NO: 13), LPIX-16 (SEQ ID NO:18), LPIX-17 (SEQ ID NO:19), and LPIX-20 (SEQ ID NO:22);

LPIX-4 (SEQ ID NO:6), LPIX-11 (SEQ ID NO: 13), and LPIX-20 (SEQ ID NO:22);

LPIX-4 (SEQ ID NO:6), LPIX-16 (SEQ ID NO:18), and LPIX-20 (SEQ ID NO:22);

LPIX-4 (SEQ ID NO:6), LPIX-17 (SEQ ID NO:19), and LPIX-20 (SEQ ID NO:22);

LPIX-5 (SEQ ID NO:7), LPIX-11 (SEQ ID NO: 13), and LPIX-20 (SEQ ID NO:22);

LPIX-5 (SEQ ID NO:7), LPIX-16 (SEQ ID NO:18), and LPIX-20 (SEQ ID NO:22);

LPIX-11 (SEQ ID NO: 13), LPIX-16 (SEQ ID NO:18), and LPIX-20 (SEQ ID NO:22);

LPIX-11 (SEQ ID NO: 13), LPIX-17 (SEQ ID NO:19), and LPIX-20 (SEQ ID NO:22);

LPIX-16 (SEQ ID NO:18), LPIX-17 (SEQ ID NO:19), and LPIX-20 (SEQ ID NO:22).

In yet another aspect of the present invention, a composition is provided comprising at least two peptides (e.g., a physical mixture of at least two peptides), each comprising at least one T cell epitope of Lol p V. Such compositions can be in the form of a composition additionally with a pharmaceutically acceptable carrier of diluent for therapeutic uses, or with conventional non-pharmaceutical excipients for reagent use. When used therapeutically, an effective amount of one or more of such compositions can be administered simultaneously or sequentially to an individual sensitive to ryegrass pollen.

In another aspect of the invention, combinations of Lol p V peptides are provided which can be administered simultaneously or sequentially. Such combinations may comprise therapeutic compositions comprising only one peptide, or more peptides if desired. Such compositions may be used simultaneously or sequentially in preferred combinations.

Preferred compositions and preferred combinations of Lol p V peptides which can be administered or otherwise used simultaneously or sequentially (comprising peptides having amino acid sequences shown in FIG. 2) include the following combinations:

LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), and LPIX-20 (SEQ ID NO:22);

LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), and LPIX-20 (SEQ ID NO:22);

LPIX-4 (SEQ ID NO:6), LPIX-5 (SEQ ID NO:7), LPIX-6 (SEQ ID NO:8), LPIX-17 (SEQ ID NO:19) and LPIX-20 (SEQ ID NO:22);

LPIX-4 (SEQ ID NO:6), LPIX-5 (SEQ ID NO:7), LPIX-6 (SEQ ID NO:8) and LPIX-20 (SEQ ID NO:22);

LPIX-4 (SEQ ID NO:6), LPIX-5 (SEQ ID NO:7), LPIX-6 (SEQ ID NO:8), LPIX-11 (SEQ ID NO: 13), LPIX-12 (SEQ ID NO:14), LPIX-16 (SEQ ID NO:18), LPIX-17 (SEQ ID NO:19) and LPIX-20 (SEQ ID NO:22);

LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25) and LPIX-26 (SEQ ID NO:28);

LPIX-4 (SEQ ID NO:6), LPIX-11 (SEQ ID NO: 13), LPIX-16 (SEQ ID NO:18), and LPIX-20 (SEQ ID NO:22);

LPIX-4 (SEQ ID NO:6), LPIX-11 (SEQ ID NO: 13), LPIX-17 (SEQ ID NO:19), and LPIX-20 (SEQ ID NO:22);

LPIX-4 (SEQ ID NO:6), LPIX-16 (SEQ ID NO:18), LPIX-17 (SEQ ID NO:19), and LPIX-20 (SEQ ID NO:22);

LPIX-5 (SEQ ID NO:7), LPIX-11 (SEQ ID NO: 13), LPIX-16 (SEQ ID NO:18), and LPIX-20 (SEQ ID NO:22);

LPIX-5 (SEQ ID NO:7), LPIX-11 (SEQ ID NO: 13), LPIX-17 (SEQ ID NO:19), and LPIX-20 (SEQ ID NO:22);

LPIX-5 (SEQ ID NO:7), LPIX-16 (SEQ ID NO:18), LPIX-17 (SEQ ID NO:19), and LPIX-20 (SEQ ID NO:22);

LPIX-11 (SEQ ID NO: 13), LPIX-16 (SEQ ID NO:18), LPIX-17 (SEQ ID NO:19), and LPIX-20 (SEQ ID NO:22);

LPIX-4 (SEQ ID NO:6), LPIX-11 (SEQ ID NO: 13), and LPIX-20 (SEQ ID NO:22);

LPIX-4 (SEQ ID NO:6), LPIX-16 (SEQ ID NO:18), and LPIX-20 (SEQ ID NO:22);

LPIX-4 (SEQ ID NO:6), LPIX-17 (SEQ ID NO:19), and LPIX-20 (SEQ ID NO:22);

LPIX-5 (SEQ ID NO:7), LPIX-11 (SEQ ID NO: 13), and LPIX-20 (SEQ ID NO:22);

LPIX-5 (SEQ ID NO:7), LPIX-16 (SEQ ID NO:18), and LPIX-20 (SEQ ID NO:22);

LPIX-11 (SEQ ID NO: 13), LPIX-16 (SEQ ID NO:18), and LPIX-20 (SEQ ID NO:22);

LPIX-11 (SEQ ID NO: 13), LPIX-17 (SEQ ID NO:19), and LPIX-20 (SEQ ID NO:22);

LPIX-16 (SEQ ID NO:18), LPIX-17 (SEQ ID NO:19), and LPIX-20 (SEQ ID NO:22).

In another aspect of the present invention, a therapeutic composition is provided comprising at least two peptides (e.g. a physical mixture of at least two peptides, each peptide comprising at least one epitope) wherein at least one peptide, comprises an amino acid sequence or portion thereof derived from Lol p V selected from the following group: LPIX-1 (SEQ ID NO:3), LPIX-2 (SEQ ID NO:4), LPIX-3 (SEQ ID NO:5), LPIX-4 (SEQ ID NO:6), LPIX-5 (SEQ ID NO:7), LPIX-6 (SEQ ID NO:8), LPIX-7 (SEQ ID NO:9), LPIX-8 (SEQ ID NO:10), LPIX-9 (SEQ ID NO:11), LPIX-10 (SEQ ID NO:12), LPIX-11 (SEQ ID NO:13), LPIX-12 (SEQ ID NO:14), LPIX-13 (SEQ ID NO:15), LPIX-14 (SEQ ID NO:16), LPIX-15 (SEQ ID NO:17), LPIX-16 (SEQ ID NO:18), LPIX-17 (SEQ ID NO:19), LPIX-18 (SEQ ID NO:20), LPIX-19 (SEQ ID NO:21), LPIX-20 (SEQ ID NO:22), LPIX-21 (SEQ ID NO:23), LPIX-22 (SEQ ID NO:24), LPIX-23 (SEQ ID NO:25), LPIX-24 (SEQ ID NO:26), LPIX-26 (SEQ ID NO:28), and LPIX-27 (SEQ ID NO:29) (as shown in FIG. 2), and wherein at least one peptide comprises an amino acid sequence or portion thereof derived from Lol p I selected from the following group: LPI-1 (SEQ ID NO:30), LPI-1.1 (SEQ ID NO:31), LPI-2 (SEQ ID NO:32), LPI-3 (SEQ ID NO:55), LPI-4 (SEQ ID NO:33), LPI-4.1 (SEQ ID NO:34), LPI-5 (SEQ ID NO:35), LPI-6 (SEQ ID NO:36), LPI-7 (SEQ ID NO:37), LPI-8 (SEQ ID NO:38), LPI-9 (SEQ ID NO:39), LPI-10 (SEQ ID NO:40), LPI-11 (SEQ ID NO:41), LPI-12 (SEQ ID NO:42), LPI-13 (SEQ ID NO:43), LPI-14 (SEQ ID NO:44), LPI-15 (SEQ ID NO:45), LPI-16 (SEQ ID NO:46), LPI-16.1 (SEQ ID NO:47), LPI-17 (SEQ ID NO:48), LPI-18 (SEQ ID NO:49), LPI-19 (SEQ ID NO:50), LPI-20 (SEQ ID NO:56), LPI-21 (SEQ ID NO:51), LPI-22 (SEQ ID NO:52), and LPI-23 (SEQ ID NO:53) (as shown in FIG. 3). The isolation and cloning of the clones encoding Lol p I as well as the synthesis of the various Lol p I peptides shown in FIG. 3, along with human T cell studies using Lol p I and using various peptides derived from Lol p I are described in PCT/US94/02537, which is hereby incorporated by reference in its entirety.

Preferably, a therapeutic composition comprises at least five, six, seven, or eight peptides wherein at least three or four peptides are derived from Lol p V and are selected from the following group: LPIX-4 (SEQ ID NO:6), LPIX-5 (SEQ ID NO:7), LPIX-11 (SEQ ID NO: 13), LPIX-16 (SEQ ID NO:18), LPIX-17 (SEQ ID NO:19), and LPIX-20 (SEQ ID NO:22), and at least two, three or four peptides are derived from Lol p I and selected from the following group: LPI-16 (SEQ ID NO:46), LPI-18 (SEQ ID NO:49), LPI-20 (SEQ ID NO:56), and LPI-23 (SEQ ID NO:53); for example, a preferred therapeutic composition comprises at least two peptides of Lol p I and three peptides of Lol p V, or three peptides from Lol p I and three peptides from Lol p V, or three peptides from Lol p I and four peptides from Lol p V, or four peptides from Lol p I and four peptides from Lol p V, or four peptides from Lol p I and three peptides from Lol p V.

In another aspect of the present invention a method is provided comprising administering a combination of peptides or portions thereof derived from Lol p V and Lol p I which can be administered simultaneously or sequentially; each of such peptides can be in the form of a therapeutic composition with a pharmaceutically acceptable carrier or diluent. Examples of preferred compositions and preferred combinations comprising Lol p V and Lol p I peptides or portions thereof, which can be administered simultaneously or sequentially comprise the following combinations:

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25), LPIX-26 (SEQ ID NO:28);

LPI-16.1 (SEQ ID NO:47), LPI-18 (SEQ ID NO:49), LPI-20, LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25), LPIX-26 (SEQ ID NO:28), LPIX-4 (SEQ ID NO:6), LPIX-5 (SEQ ID NO:7), LPIX-6 (SEQ ID NO:8), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52), LPIX-4 (SEQ ID NO:6), LPIX-5 (SEQ ID NO:7), LPIX-6 (SEQ ID NO:8), LPIX-9 (SEQ ID NO:11), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52), LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPI-22 (SEQ ID NO:52);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25), LPIX-26 (SEQ ID NO:28);

LPI-16.1 (SEQ ID NO:47), LPI-18 (SEQ ID NO:49), LPI-20 (SEQ ID NO:56), LPI-23 (SEQ ID: NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-9 (SEQ ID NO:11), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-12 (SEQ ID NO:14), LPIX-16 SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-10 (SEQ ID NO:40), LPI-11 (SEQ ID NO:41), LPI-15 (SEQ ID NO:45), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22); LPIX-23 (SEQ ID NO:25), LPIX-26 (SEQ ID NO:28);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-9 (SEQ ID NO:11), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ. ID NO:52), LPIX-4 (SEQ ID NO:6), LPIX-5 (SEQ ID NO:7), LPIX-6 (SEQ ID NO:8), LPIX-8 (SEQ. ID NO:10), LPIX-9 (SEQ. ID NO:11), LPIX-11 (SEQ. ID NO:13), LPIX-12 (SEQ. ID NO:14), LPIX-16 (SEQ ID NO:18), LPIX-17 (SEQ ID NO:19), LPIX-19 (SEQ. ID NO:21), LPIX-20 (SEQ ID NO:22), LPIX-23 (SEQ. ID NO:25), LPIX-26 (SEQ. ID NO:28);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ ID NO:52), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ ID NO:52), LPIX-4 (SEQ ID NO:6), LPIX-5 (SEQ ID NO:7), LPIX-6 (SEQ ID NO:8), LPIX-9 (SEQ ID NO:11), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ ID

NO:52), LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ ID NO:52), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPI-4.1 (SEQ ID NO:34), LPI-22 (SEQ ID NO:52), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPI-3 (SEQ ID NO:55), LPIX-4 (SEQ ID NO:6), LPIX-5 (SEQ ID NO:7), LPIX-6 (SEQ ID NO:8), LPIX-8 (SEQ ID NO:10), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25), LPIX-26 (SEQ ID NO:28);

LPI-16.1 (SEQ ID NO:47), LPI-18 (SEQ ID NO:49), LPI-20 (SEQ ID NO:56), LPI-23 (SEQ ID NO:53), LPIX-4 (SEQ ID NO:6), LPIX-5 (SEQ ID NO:7), LPIX-6 (SEQ ID NO:8), LPIX-9 (SEQ ID NO:11), LPIX-11 (SEQ ID NO:13), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPIX-4 (SEQ ID NO:6), LPIX-5 (SEQ ID NO:7), LPIX-6 (SEQ ID NO:8), LPIX-9 (SEQ ID NO:11), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22), LPIX-23 (SEQ ID NO:25);

LPI-16.1 (SEQ ID NO:47), LPI-18 (SEQ ID NO:49), LPI-20 (SEQ ID NO:56), LPI-23 (SEQ ID NO:53), LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), LPIX-19 (SEQ ID NO:21), LPIX-20 (SEQ ID NO:22);

LPI-16.1 (SEQ ID NO:47), LPI-18 (SEQ ID NO:49), LPI-20 (SEQ ID NO:56), LPI-23 (SEQ ID NO:53), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-19 (SEQ ID NO:21), LPIX-20 (SEQ ID NO:22); and--.

LPI-16.1, LPI-18, LPI-20, LPI-23, LPIX-4, LPIX-5, LPIX-6, LPIX-16, LPIX-17, LPIX-20 with --LPI-16.1 (SEQ ID NO:47), LPI-18 (SEQ ID NO:49), LPI-20 (SEQ ID NO:56), LPI-23 (SEQ ID NO:53), LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), LPIX-20 (SEQ ID NO:22).

In addition, a composition is provided comprising at least two Lol p I peptides (e.g. a physical mixture of at least two peptides), each comprising at least one T cell epitope of Lol p I. Such compositions can be administered in the form of a therapeutic composition with with a pharmaceutically acceptable carrier or diluent to treat ryegrass sensitivity and particularly, sensitivity to Lol p I protein allergen. Preferred compositions and preferred combinations of Lol p I peptides which can be administered simultaneously or sequentially (comprising peptides having the amino acid sequences shown in FIG. 3 include the following combinations:

LPI-16 (SEQ ID NO:46), and LPI-20 (SEQ ID NO:56);

LPI-18 (SEQ ID NO:49), and LPI-20 (SEQ ID NO:56);

LPI-20 (SEQ ID NO:56), and LPI-23 (SEQ ID NO:53);

LPI-16 (SEQ ID NO:46), LPI-18 (SEQ ID NO:49), and LPI-20 (SEQ ID NO:56);

LPI-16 (SEQ ID NO:46), LPI-20 (SEQ ID NO:56), and LPI-23 (SEQ ID NO:53);

LPI-18 (SEQ ID NO:49), LPI-20 (SEQ ID NO:56), and LPI-23 (SEQ ID NO:53);

LPI-16 (SEQ ID NO:46), LPI-18 (SEQ ID NO:49), LPI-20 (SEQ ID NO:56), and LPI-23 (SEQ ID NO:53).

Any of the compositions described herein are useful in the manufacture of a medicament for treating sensitivity to ryegrass pollen allergen or an immunologically cross reactive allergen in an individual.

The present invention if further illustrated by the following non-limiting Figures and Examples.

EXAMPLE I

Purification of Native Lol p V from Ryegrass Pollen

A. Production and Purification of Monoclonal Antibody (mAb) 1B9.

Balb/c mice were immunized with crude *Dactylis glomerata* (orchard grass/cocksfoot grass) pollen extract and antibody secreting clones were generated as described (Walsh et al., *Int. Arch. Allergy Appl. Immunol.*, 1990, 91: 419–425). MAb 1B9 hybridoma clone which cross-reacts to Lol p V was obtained from Dr. Walker (Univ. Birmingham, Wolfson Research Lab, Birmingham, UK). Ascitis fluid generated from Balb/c mice was produced by contract (Babco, Richmond, Calif.). The antibodies were purified from ascites fluid by $(NH_4)_2 SO_4$ precipitation (50% saturation). The pellet was resuspended in 10 mM phosphate buffer, pH 7.5 and dialyzed against the same buffer at 4° C. overnight and then fractionated by ion-exchange chromatography on FPLC Q-SEPHAROSE column (Pharmacia, Piscataway, N.J.) using linear gradient 0–0.5 M NaCl. IgG was eluted between 0.15–0.2 M NaCl concentration.

B. Preparation of 1B9 Immunoaffinity Column

Purified 1B9 was coupled to AFFIGEL-10 resin (Biorad, Richmond, Calif.) using 3–4 mg protein/mL of gel according to manufacturer's instructions. In brief, PFLC Q-SEPHAROSE column purified mAb 1B9 was dialyzed against 0.1M MOPS buffer, pH 7.5 with two to three changes overnight at 4° C. The AFFIGEL-10 resin was washed with deionized cold $H_2O$ in a scintered glass funnel. The washed resin was mixed with the 1 B9 antibody for four hours at 4° C., followed by an one-hour blocking step with 1 M ethanolamine, pH 8.0. Resin was packed into a column, washed with PBS and than stored in PBS+0.05% sodium azide.

C. Affinity Purification of Lol p V from Ryegrass Pollen 100 g defatted ryegrass pollen (purchased from Greer Laboratories, Lenoir, N.C.) was extracted 1 liter extraction buffer containing 0.05 M phosphate buffer, pH 7.2, 0.15 M NaCl, phenyl methyl sulfonyl fluoride (170 µg/mL), leupeptin (1 µg/mL), pepstatin (1 µg/mL) and soybean trypsin inhibito (1 µg/mL).

The pollen was extracted by stirring the solution overnight at 4° C., followed by centrifugation 12,000×g for 100 minutes. The insoluble materials were re-extracted in 0.5–1.0L extraction buffer a then the supernatants were combined and depigmented by batch absorption onto 100 mL DE-52 cellulose (Whatman, Maidstone, England) equilibrated with 0.05 M phosphate buffer+0.3 M NaCl, 7.2.

The unbound materials were loaded onto the 1B9 AFFI-GEL-10 column at a flow rate of 0.5 ml/min. The column was then washed extensively with PBS, PBS+0.5 NaCl and once again with PBS before elution of the Lol p V allergens with 0.1 M glycine, pH 2.7. Fractions were neutralized with 1 M Tris, pH 11.0 immediately. These affinity-purified materials were used in IgE studies and T cell epitope mapping.

Physicochemical Properties of Affinity-Purified Lol p V

Figure 15:
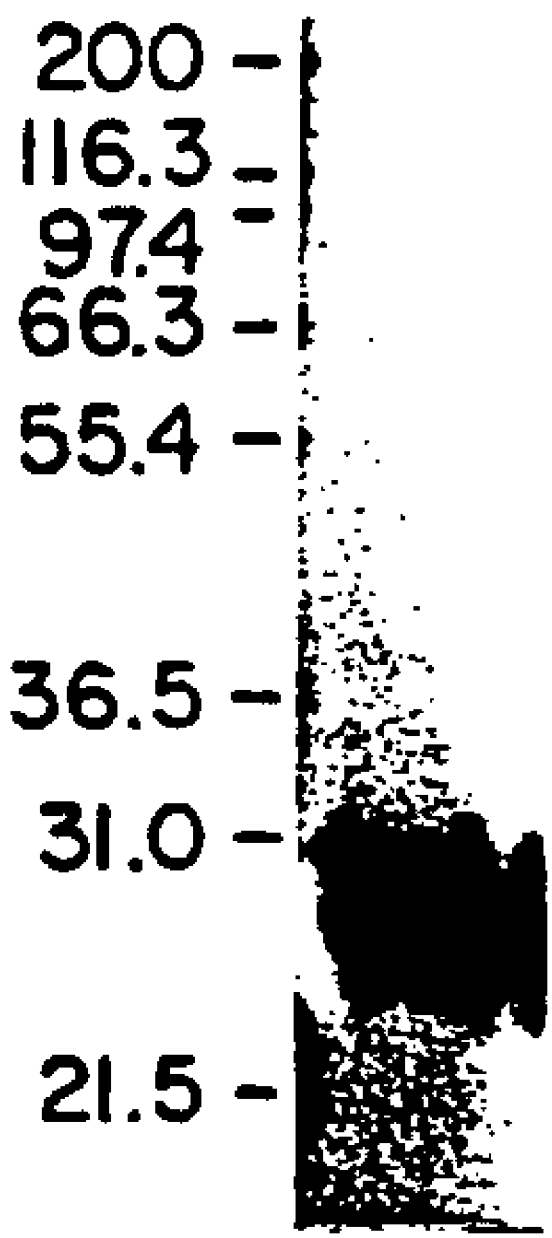
FIG. 15 is a photograph of a Coomassie blue stained SDS-PAGE (12.5%) analysis of an Ab1B9-affinity purified native Lol p V, the sample was run under reducing conditions, the molecular weight standards are shown on the left.

The 1B9 affinity-purified material was analyzed by SDS-PAGE. As shown in FIG. 15, Lol p exists as multiple bands with molecular weight ranged from 29,000–22,000. All these components were reactive with 1B9 by Western blotting analysis (data not shown). These components were electroblotted onto ProBlott membrane (Applied Biosystems, Foster City, Calif.), stained by Coomassi blue and the three major bands were excised and sequenced on a Beckman LF-3000 sequencer (Beckman Instruments, Carlsbad, Calif.). N-terminal amino acid sequence of the three bands are show Table I. The sequencing data shows that the middle and lower molecular weight bands represent N-terminal cleavage products of the higher molecular weight component. The N-terminus sequence wa identical to the cloned Lol p V (12R) (see PCT application publication number WO93/04174). The 5 proline residues at the N-terminus were found to be all hydroxyprolines, which seemed to be commo Group V allergens from Northern grasses (Matthiesen, F. et al., 1991, *Clin. Exp. Allergy*, 21:297–307 We also determined the 1B9-affinity purified material by amino acid analysis (Table 2) and the data were very similar to the Lol p V and other group V allergens from Northern grasses reported by Klys et al., (*Clin. Experimental Allergy*, 1992, 22:491–497). Furthermore, Western blot analysis using specific anti-group I mAb (data not shown) demonstrated Group I proteins could not be detected in th preparations. Thus, taken together these data suggest that the 1B9-affinity purified preparations contained only Group V allergens.

TABLE 1

N-terminal amino acid sequence and cleavage site of Lol p V allergen

| amino acid # | 1 | 11 |
|---|---|---|
| Lol p V (SEQ ID NO:54) | | |
| | ADAGYTP'AAAATP'ATP'AATP' | |
| | 21 | 31 |
| | AAAGGKATTDEQK | |

TABLE 1-continued

N-terminal amino acid sequence and cleavage site of Lol p V allergen

P' represents hydroxyproline
The N-terminal sequence was determined from the three major bands electroblotted onto ProBlott membrane. The upper band starts with amino acid 1 whereas the middle and the lower bands start at amino acid 9 and 18, respectively. The arrows indicate the cleavage sites.

TABLE 2

Amino acid composition of Group V allergens

| | | | Mole % | | |
|---|---|---|---|---|---|
| | | | | Lol p V[b] | |
| Amino acid | Phl p V[a] | Lol p V[a] | expt 1 | expt 2 | expt 3 |
| Asx | 5.4 | 6.3 | 5.3 | 6.7 | 7.5 |
| Thr | 7.6 | 8.6 | 7.4 | 8.7 | 9.2 |
| Ser | 5.1 | 2.0 | 3.3 | 2.3 | 2.7 |
| Glx | 10.2 | 9.8 | 7.4 | 8.8 | 8.9 |
| Gly | 6.4 | 4.0 | 7.2 | 5.2 | 4.8 |
| Ala | 25.7 | 29.0 | 27.7 | 31.3 | 31.7 |
| Cys | 0.0 | 1.0 | — | — | — |
| Val | 6.6 | 6.4 | 5.5 | 5.5 | 6.4 |
| Met | 0.7 | 0.3 | 0.5 | 0.3 | 0.8 |
| Ile | 3.6 | 3.4 | 3.5 | 2.9 | 3.1 |
| Leu | 4.7 | 5.9 | 6.5 | 5.0 | 5.3 |
| Tyr | 3.5 | 3.0 | 2.9 | 2.5 | 1.7 |
| Phe | 4.1 | 5.0 | 4.8 | 4.0 | 4.5 |
| His | 0.8 | 0.3 | — | 0.2 | 0.5 |
| Lys | 8.8 | 9.8 | 11.0 | 9.2 | 6.0 |
| Arg | 1.0 | 0.4 | 0.6 | 0.4 | 0.8 |
| Pro | 4.5 | 4.9 | 5.4[c] | 4.7[c] | 3.7[c] |
| Hyp | 1.4 | N.R. | 1.5[c] | 1.8[c] | 1.7[c] |

N.R. (Not reported)
[a]values reported by Klysner, S. et al. Clin. Exp. Allergy (1992) 22: 491–497.
[b]the amino acid composition was determined from mAb 1B9-affinity purified materials and values obtained from three experiments are presented.
[c]the content of proline and hydroxyproline was determined by peak height since the hydroxyproline peak was very broad due to an contaminant which eluted at the trailing edge of the hydroxyproline peak. All the other amino acids were determined by peak areas.

EXAMPLE 2

Human T Cell Studies with Lol p V

Synthesis of Overlapping Peptides

The amino acid sequence of Lol p V was deduced from the cDNA sequence of clone 12R (SEQ ID NO:2) ATCC number 69475 as shown in FIG. 1. The details of the isolation and cloning of clone 12R encoding Lol p V (described as Lol p Ib.1) are given in PCT application publication number WO93/04174 incorporated herein by reference in its entirety. One example of expression of recombinantly produced Lol p V encoded by clone 12R is given in Example 4, to follow.

Ryegrass Lol p V overlapping peptides were synthesized using standard Fmoc/tBoc synthetic chemistry and purified by Reverse Phase HPLC. FIG. 2 shows Lol p V peptides used in these studies. The peptide names are consistent throughout.

T Cell Responses to Ryegrass Antigen Peptides

Peripheral blood mononuclear cells (PBMC) were purified by lymphocyte separation medium (LSM) centrifugation of 60 ml of heparinized blood from grass-allergic patients who exhibited clinical symptoms of seasonal rhinitis and were skin test positive for grass. Long-term T cell lines were established by stimulation of $2\times10^6$ PBL/ml in bulk cultures of complete medium (IRPMI-164), 2 mM L-glutamine, 100 U/ml penicillin/streptomycin, $5\times10^{-5}$M 2-mercaptoethanol, and 10 mM HEPES, supplemented with 5% heat-inactivated human AB serum, with 10 μg/ml of affinity purified native Lol p V for 6 days at 37° C. in a humidified 5% $CO_2$ incubator to select for Lol p V reactive T Cells. This amount of priming antigen was determined to be optimal for the activation of T cells from most grass-allergic patients. Viable cells were purified by LSM centrifugation and cultured in complete medium, supplemented with 5 units recombinant human IL-2/ml and 5 units recombinant human IL-4/ml for up to 3 weeks until the desired cell number were achieved. The cells were allowed to rest for 4–6 days.

The ability of the T cells to proliferate to selected peptides, recombinant Lol p I (rLol p I), purified native Lol p V, purified rLol p V, or recombinant Fel d I (rFel d I) (chain I), or tetanus toxoid (TT) was then assessed. For assay, $2\times10^4$ rested cells were restimulated in the presence of $2\times10^4$ autologous Epstein-Barr virus (EBV)-transformed B cells (prepared as described below) or $5\times10^4$ irradiated PBL with 2–50 mg/ml of rLol p I, purified native Lol p V, rFel d I (Chain I), or rLol p I, in a volume of 200 ml complete medium in duplicate wells in 96-well round-bottom plates for three days. Each well then received 1 mCi tritiated thymidine for 16–20 hours. The counts incorporated were collected onto glass fiber filter mats and processed for liquid scintillation counting. The varying antigen dose in assays with rLol p V, purified native Lol p V, and recombinant Lol p I and antigenic peptides synthesized as described above were determined. The titrations were used to optimize the dose of peptides in T cell assays. The maximum response in a titration of each peptide is expressed as the stimulation index (S.I.). The S.I. is the counts per minute (CPM) incorporated by cells in response to peptide, divided by the CPM incorporated by cells in medium only. An S.I. value equal to or greater than 2 times the background level is considered "positive" and indicates that the peptide contains a T cell epitope. The positive results were used in calculating mean stimulation indices for each peptide for the group of patients tested. The results (not shown) demonstrate that one patient responds well to recombinant Lol p V and purified native Lol p V, as well as to Lol p V peptides but not to rFel d I (Chain I) or TT. This indicated that Lol p V T cell epitopes are recognized by T cells from this particular allergic patient and that rLol p V contains such T cell epitopes.

The above procedure was followed with a total of 19 patients. Individual patient results were used in calculating the mean S.I. for each peptide if the patient responded to the purified native Lol p V protein at an S.I. of 2.0 or greater and the patient responded to at least one peptide derived from purified native Lol p I at an S.I. of 2.0 or greater. A summary of positive experiments from 19 patients is shown in FIG. 4. The numbers above each bar report the mean S.I. for that peptide. The numbers enclosed in the parentheses denote percentage of patients responding to that particular peptide. The bar represents the positivity index for each peptide (% of patients responding multiplied by mean S.I.).

FIG. 5 shows the ranked sum for each peptide derived from the same data as described above. The bar represents the cumulative rank of the peptide response in the group of the 19 patients tested. To determine the cumulative rank, the 5 peptides with the highest S.I. in each individual are determined and assigned a numerical rank in descending order, with 5 representing the strongest response. The ranks for each peptide were then summed for the entire group of patients to determine the cumulative rank for the peptide. Above each bar is the mean S.I. and percent of positive responses (in parenthesis) with an S.I. of at least 2 to the peptide in the group of 19 patients tested. Given the percent positive and the mean T cell stimulation index, the positivity index (P.I.) for each peptide can be calculated by multiplying the two numbers. FIG. 5 shows that LPIX-20 has the highest ranked sum of the peptides in this study.

EXAMPLE 3

Lol p V as a Major Ryegrass Pollen Allergen

A) ELISA Analysis

To examine the importance of Lol p V, both direct and competition ELISA assays were performed. In the direct ELISA, 100 μl of 10 μg/ml of antigen in Phosphate Buffered Saline, pH 7.4 (PBS) was used to coat Immulon II (Dynatech, Chantilly, Va.) 96 well plates for 4 hours at room temperature (RT) or overnight (O/N) at 4° C. In between each step the plates were washed 3× with PBS-T. The excess coating antigen(s) was removed and the wells blocked with 300 μl/well 0.5% gelatin +1 mg/ml PVP in PBS for 1 hour at RT. Serially diluted patient plasma or the diluent PBS+ 0.05% Tween$^{-20}$ was incubated in at 100 μl/well in duplicate wells overnight at 4° C. Unbound antibody was removed, and the wells incubated with 100 l/well of 2nd Ab (1:1000, biotinylated goat anti-human IgE, KPL Inc., Gaithersburg, Md.) for 1 hour at RT. This solution was removed and streptavidin-horse radish peroxidase (HRPO) (1:10000) was added at 100 μl/well (SBA Inc., Birmingham, Ala.) and incubated for 1 hr at RT. 3, 3', 5,5'-tetramethylbenzidine (TMB) Substrate (KPL, Gaithersburg, Md.) was freshly mixed and added at 100 μl/well and the color allowed to develop for 1–5 minutes. The reaction was stopped by the addition of 100 μl/well 1M phosphoric acid. Plates were read on a MR7000 plate reader (Dynatech, Chantilly, Va.) with a 450 nm filter. The absorbance levels of duplicate wells were averaged. The results were graphed as absorbance vs. dilution. The competition ELISA were carried out using the same protocol with the following changes: a single dilution of patient plasma (or pooled human plasma (PHP)) was used as the source of IgE; serially diluted antigen was mixed with the plasma and allowed to incubate O/N at 4° C. This plasma was then incubated on duplicate wells. The results are plotted as the absorbance vs. the log of the concentration of competing antigen.

Figure 6:
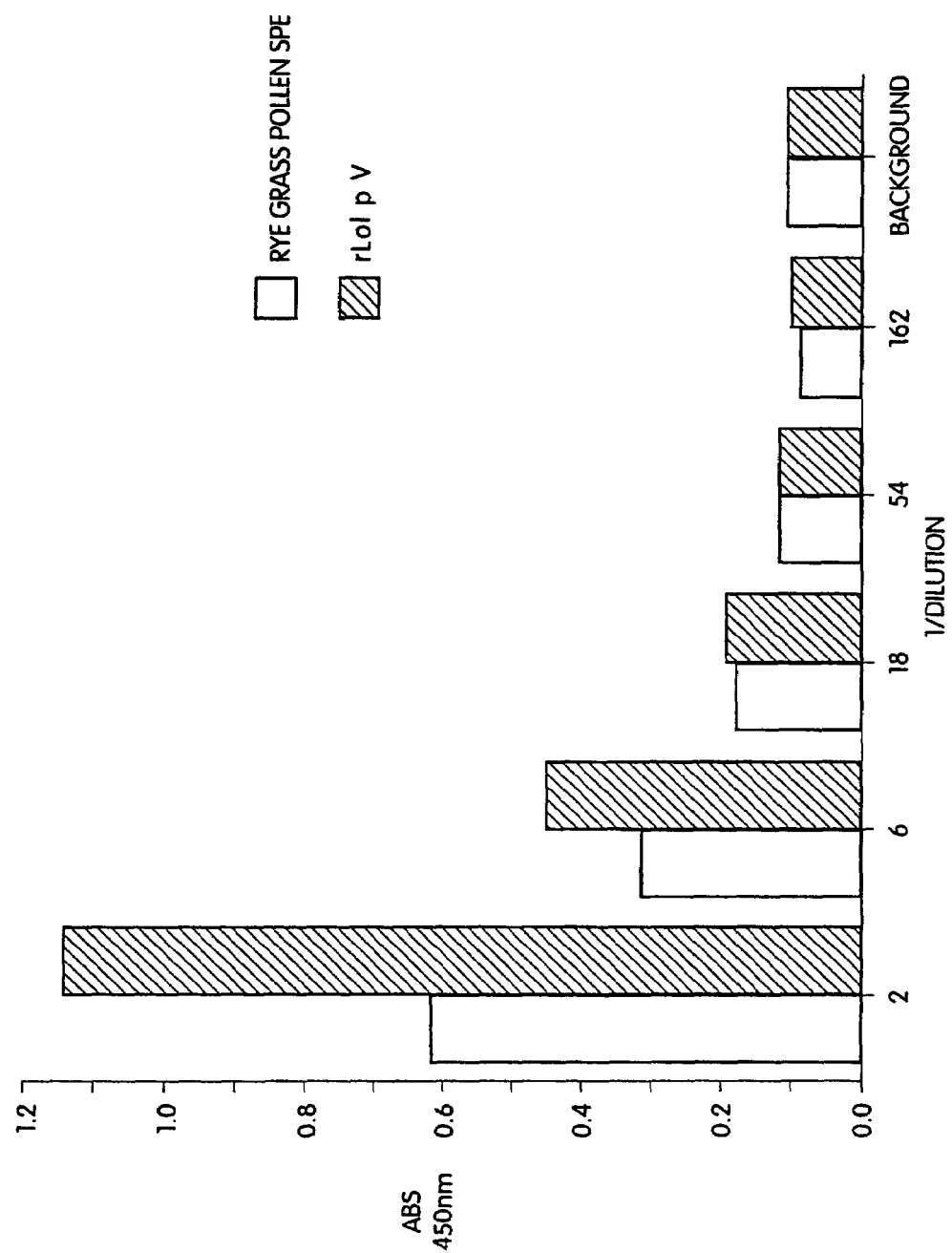
FIG. 6 is a graphic representation of the results of a direct ELISA, the source of IgE was a sample of pooled human plasma (PHP) designated PHP-A, and wherein the antigen is either soluble pollen extract (SPE) of ryegrass pollen, or bacterially expressed recombinant Lol p V (rLolpV).
Figure 7:
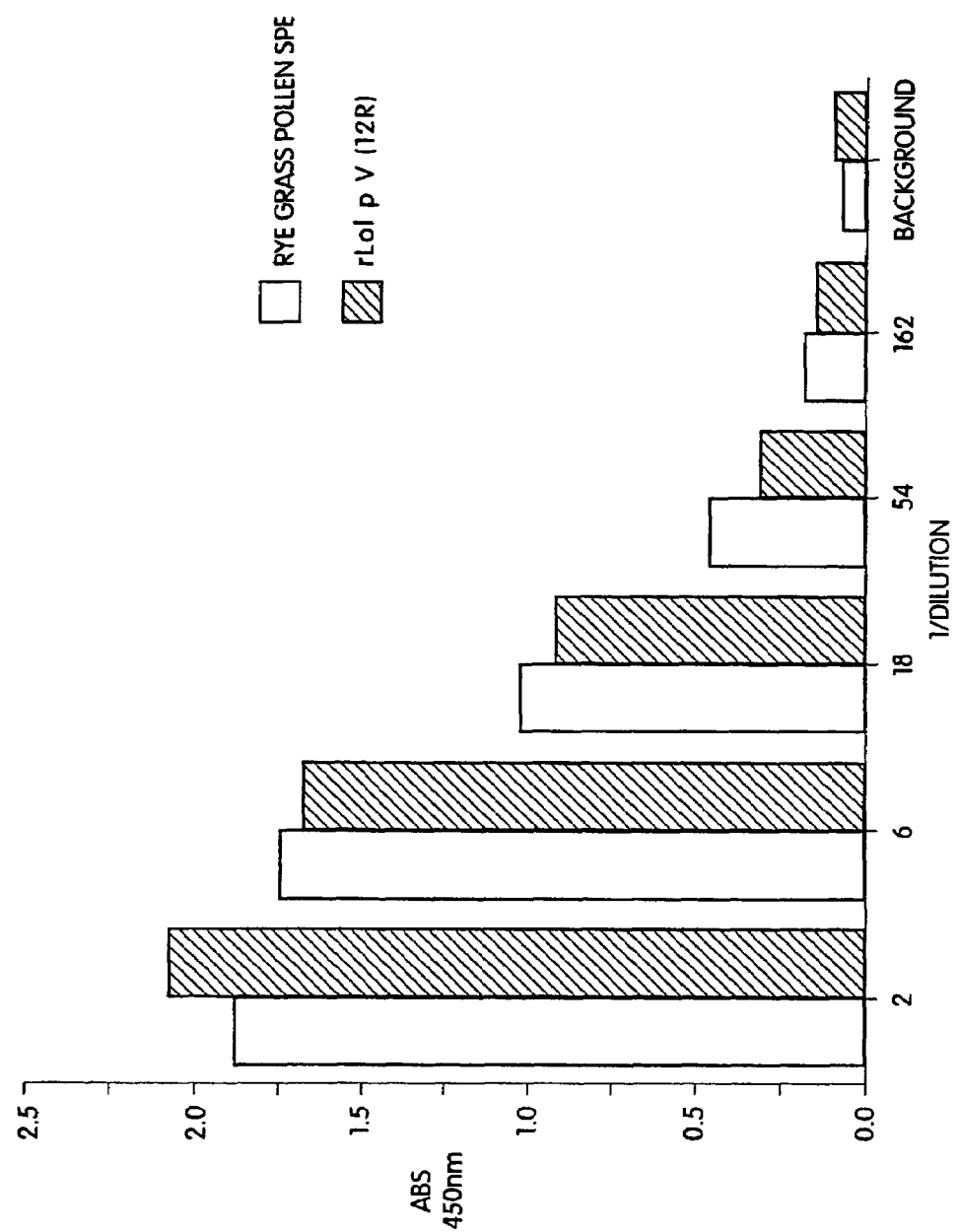
FIG. 7 is a graphic representation of the results of a direct ELISA, the source of IgE was a sample of pooled human plasma (PHP) designated PHP-B and wherein the antigen is either soluble pollen extract (SPE) of ryegrass pollen, rLol pV.
Figure 8:
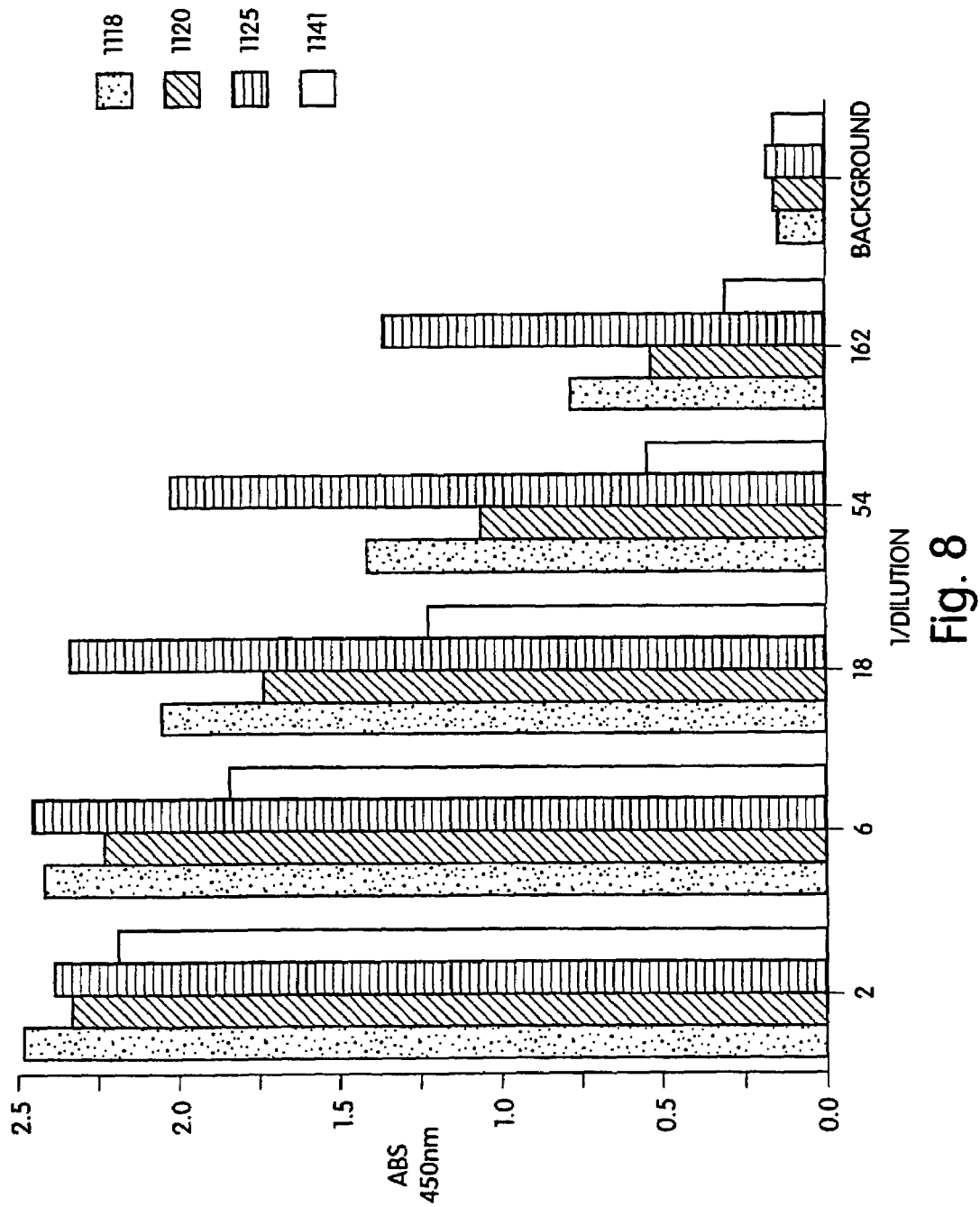
FIG. 8 is a graphic representation of the results of a direct ELISA, the source of IgE was plasma from 4 individual patients, #1118, #1120, #1125, #1141, and wherein the antigen is ryegrass pollen SPE.
Figure 9:
FIG. 9 is a graphic representation of the results of a direct ELISA the source of IgE was plasma from 4 individual patients, #1118, #1120, #1125, #1141, and wherein the antigen is rLol p V.

For the direct ELISA, wells were coated with either soluble pollen extract (SPE) of ryegrass pollen or rLol p V (purified native Lol p V may have a small amount of Lol p I; use of recombinant material assures that the IgE binding is only to Lol p V) and human IgE antibody binding to these antigens was analyzed. PHP, consisting of an equal volume of plasma from 20 patients with a ryegrass prick test score of 3+ or greater (PHP-A), or PHP consisting of equal aliquots of plasma from 40 grass skin test reactive patients with high IgE binding as measured by direct ELISA (PHP-B), or plasma from individual patients were compared in this assay. The results of binding reactivity with PHP-A (FIG. 6), PHP-B (FIG. 7), four individual patients on ryegrass pollen SPE (FIG. 8), and purified rLol p V (FIG. 9) to either SPE or rLol p V, indicate that there is high IgE binding to both the pollen extract and the recombinant protein.

Figure 10:
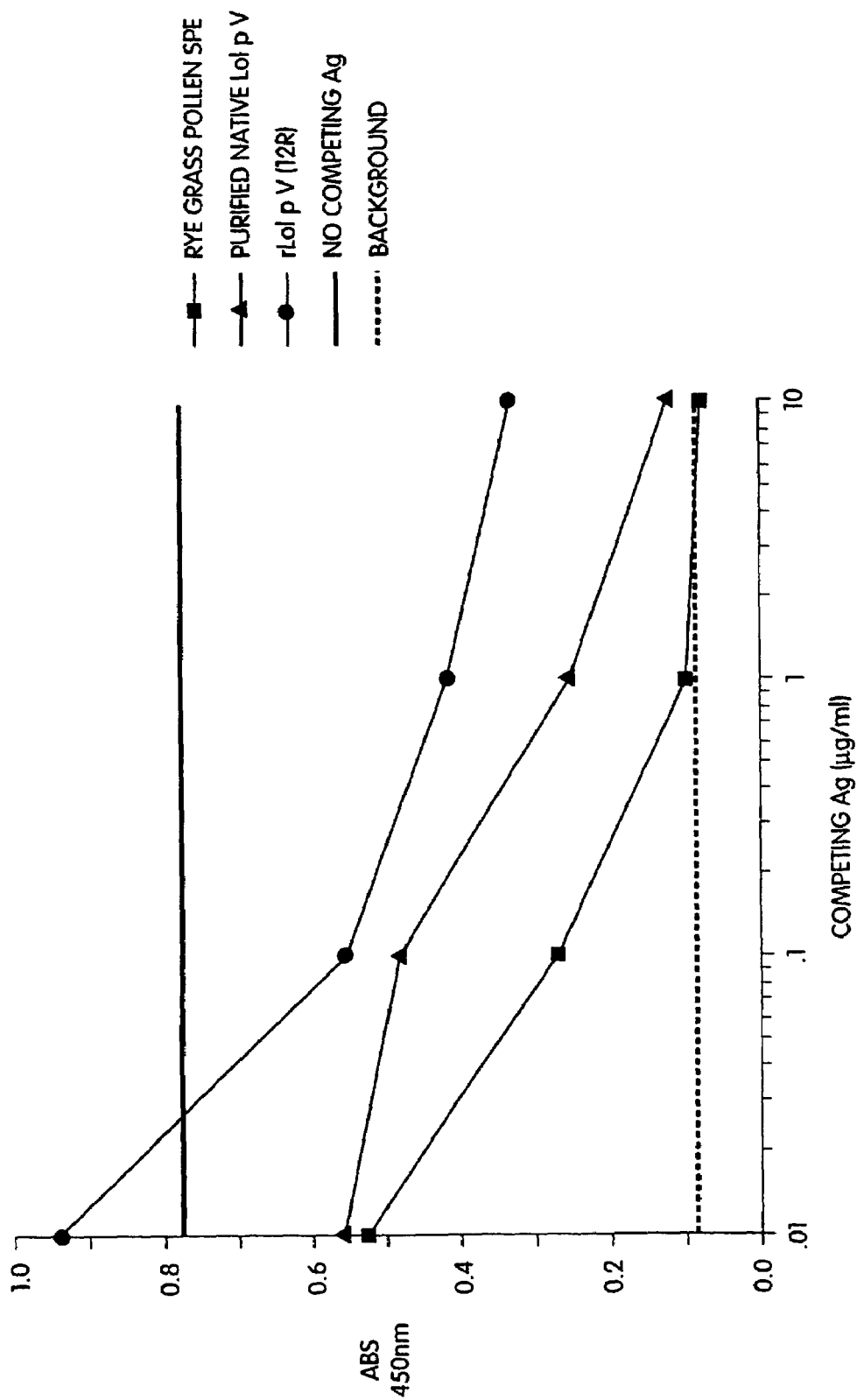
FIG. 10 is a graphic representation of the results of a competition ELISA, the source of IgE was a sample of pooled human plasma designated PHP-A, IgE binding was measured in the presence of ryegrass pollen SPE, affinity purified native Lol p V or rLol p V.
Figure 11:
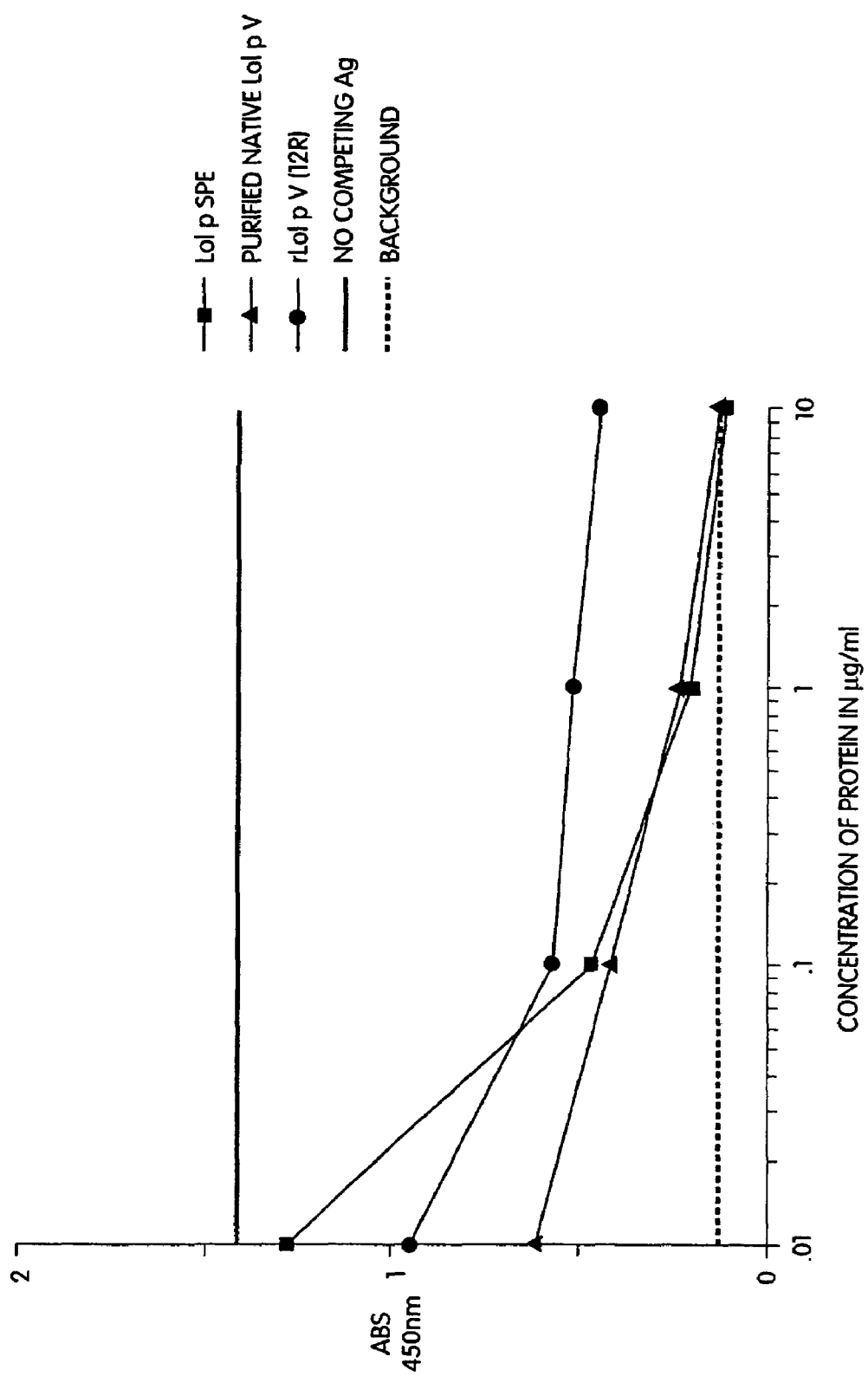
FIG. 11 is a graphic representation of the results of a competition ELISA, the source of IgE was plasma from individual patient #706 as a source of IgE, IgE binding was measured in the presence of ryegrass pollen SPE, affinity purified Lol p V or rLol p V.

In the competition assay, ELISA wells were coated with ryegrass pollen SPE and then allergic patient IgE binding was measured in the presence of competing ryegrass pollen SPE, purified native Lol p V, or rLol p V. The source of allergic IgE in this assay was PHP-A (FIG. 10) or individual patient plasma (FIG. 11). The competition assays confirm that a significant portion of IgE against Lol p SPE is specific for Lol p V.

B) Histamine Release Analysis

Figure 12:
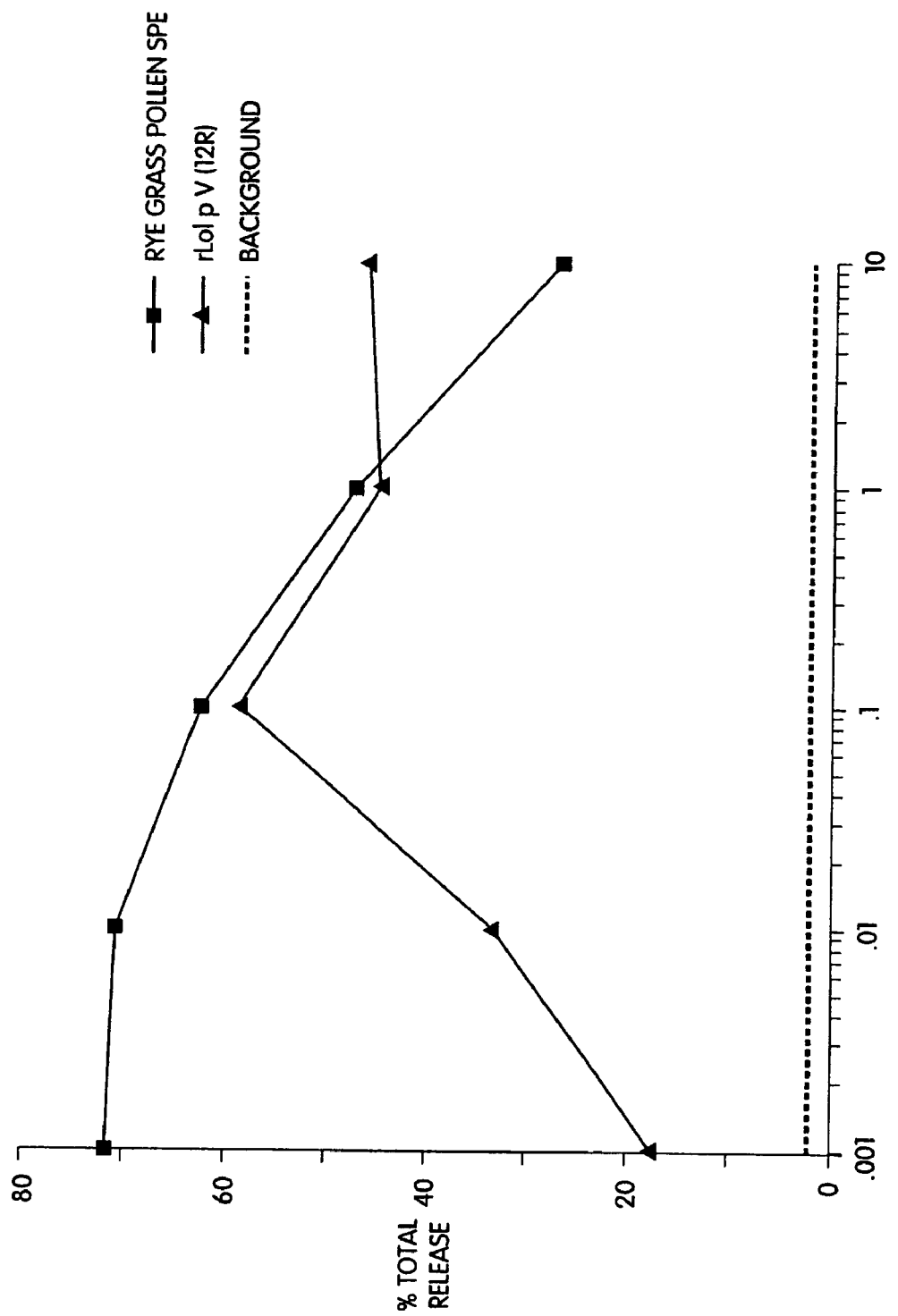
FIG. 12 is a graphic representation of a histamine release assay to ryegrass pollen SPE and rLol p V.

A histamine release assay was performed on one ryegrass allergic individual, using Lol p SPE and rLol p V as the added antigens. This assay is a measure of IgE reactivity through human basophil mediator release, and it is based on the detection of an acylated derivative of histamine using a specific monoclonal antibody (Morel, A. M. and Delaage, M. A.; 1988, J. Allergy Clin. Immunol. 82: 646–654). The reagents for this radioimmunoassay are sold as a kit by Amac Inc. (Westbrook, Me.). Whole heparinized blood drawn from a grass allergic individual and then 20011 aliquots were mixed with an equal amount of the grass antigens SPE and rLol p V at various concentrations or the diluent, PACM buffer (25 mM PIPES, 100 mM NaCl, 5 mM KCL, 4 mM $CaCl_2$, 1 mM $MgCl_2$, 0.003% HSA, pH7.3) in 1.5 ml polypropylene. The release reactions were carried out at 37° C. for 30 minutes. After this incubation the samples were centrifuged at 1500 RPM for 3 minutes and the supernatants removed. For the total histamine release, 0.1 ml of blood was added to 0.9 ml of PACM buffer, vortexed, and then boiled for 3 minutes. The samples were spun at 13000 RPM and the supernatant removed for analysis. Duplicate samples were used to measure total release. All of the supernatants are diluted 1:4 in acylation buffer and the remainder of the assay is performed according to the manufacturer's instructions. The results of this assay, shown in FIG. 12, demonstrate strong histamine release over a wide concentration range for both the extract and the recombinant protein.

C) Reactivity to Lol p V Peptides

Figure 13B:
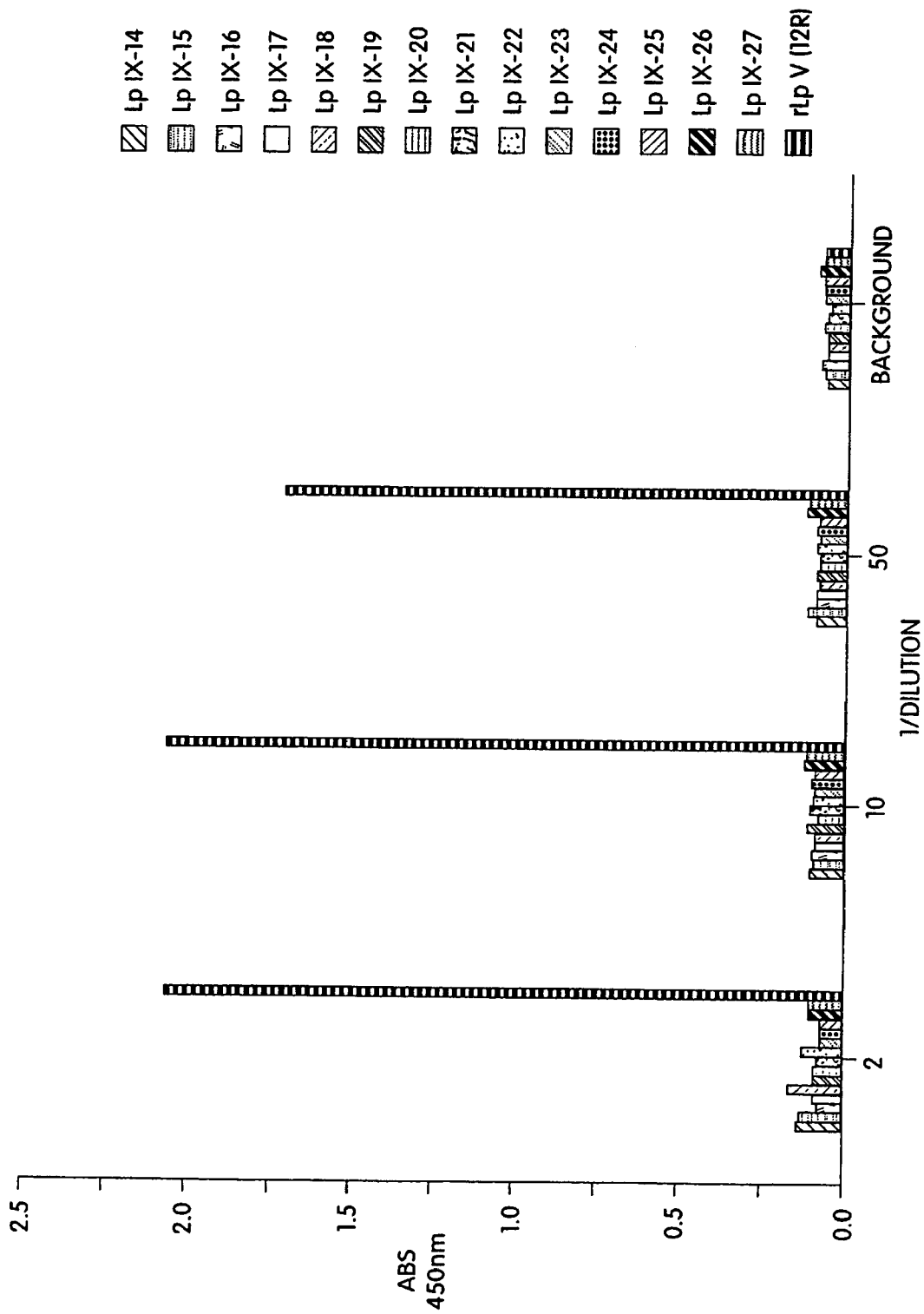

Direct ELISA was performed to assess the IgE reactivity to Lol p V peptides. In this assay ELISA plates were coated with the set of synthetic Lol p V peptides (as shown in FIG. 2) and rLol p V protein. Human IgE binding of PHP-B was incubated on the wells and the resulting binding analyzed. As evidenced in FIG. 13a and FIG. 13b there is no significant binding detected to any of the Lol p V peptides in this preliminary assay although there is very high IgE binding to Lol p V protein.

D) Lol p I and Lol p V Constitute the Major Allergens of Ryegrass Pollen

Figure 14:
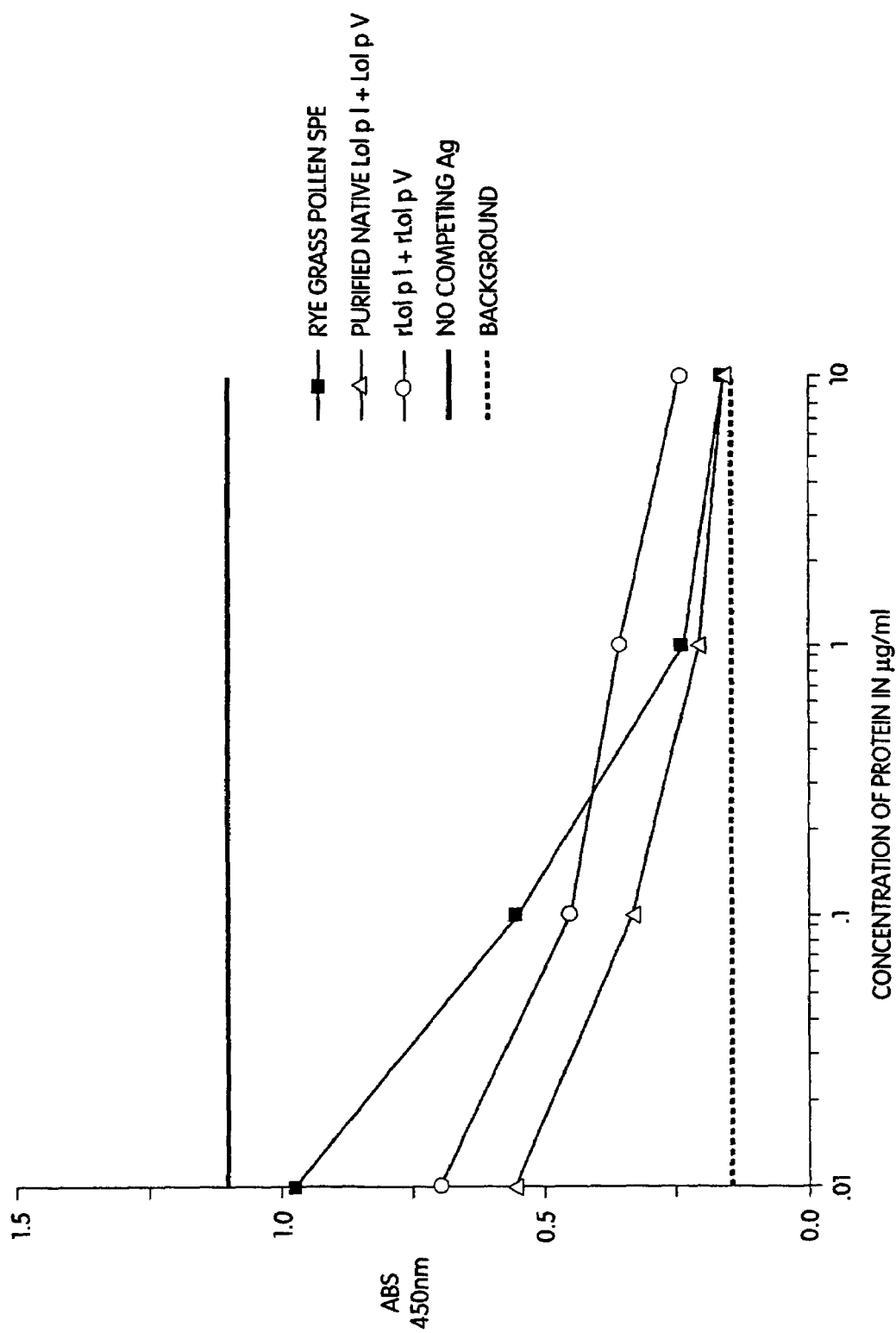
FIG. 14 is a graphic representation of a competition ELISA using a sample of pooled human plasma designated PHP-B as a source of IgE, and wherein the antigens were a mixture of affinity purified Lol p I and Lol p V or a mixture of recombinant Lol p I (rLol p I) or rLol p V to compete for IgE binding to ryegrass pollen SPE.

A separate competition ELISA was done to show that Lol p I and Lol p V together constitute the major IgE binding proteins of ryegrass pollen SPE. In this assay (FIG. 14), PHP-B was used to examine the ability of a mixture of native purified Lol p I and Lol p V or a mixture of rLol p I and rLol p V to compete for IgE binding to ryegrass pollen SPE. The mixture of purified native proteins competes to background level the IgE binding to ryegrass pollen SPE. The mixture of rLol p I and rLol p V is also able to substantially reduce the amount of IgE available to bind to the SPE coating the plate. The majority of human IgE directed against all of the ryegrass pollen proteins was bound up by the mix of just two proteins (Lol p I and Lol p V) found in the complex mix of ryegrass pollen SPE proteins. This data implies that these two proteins are major allergens of ryegrass pollen.

EXAMPLE 4

Expression of Lol p V

Expression of Lol p V was performed as follows. The λgtII clone 12R was digested with EcoRI. The insert encoding Lol p V was ligated into pGEX. A pGEX vector containing Lol p V (clone 12R) was digested with EcoRI. The Lol p V insert (containing the nucleotide sequence shown in FIG. 1) was isolated by electrophoresis of this digest through a 1% SeaPlaque low melt agarose gel. The insert was then ligated into EcoRI digested expression vector pET-11d (Novagen, Madison, Wis.; Jameel et al. (1990) J. Virol. 64:3963–3966) modified to contain a sequence encoding 6 histidines (His 6) immediately 3' of the ATG initiation codon followed by a unique EcoR I endonuclease restriction site. A second EcoR I endonuclease restriction site in the vector, along with neighboring Cla I and Hind III endonuclease restriction sites, had previously been removed by digestion with EcoR I and Hind III, blunting and religation. The histidine ($His_6$) sequence was added for affinity purification of the recombinant protein (rLol p V) on a $Ni^{2+}$ chelating column (Hochuli et al. (1987) J. Chromatog. 411:177–184; Hochuli et al. (1988) Bio/Tech. 6:1321–1325.). A recombinant clone was used to transform Escherichia coli strain BL21-DE3 which harbors a plasmid that has an isopropyl-β-D-thiogalactopyranoside (IPTG)-inducible promoter preceding the gene encoding T7 polymerase. Induction with IPTG leads to high levels of T7 polymerase expression, which is necessary for expression of the recombinant protein in pET-11d, which has a T7 promoter. The pET-11d containing the Lol p V (clone 12R) was confirmed by dideoxy sequencing (Sanger et al., (1977) Proc. Natl. Acad. Sci., (USA) 74:5460–5463) to be a Lol p V clone in the correct reading frame for expression.

The pET-11d Lol p V clone was grown on a large scale for recombinant protein expression and purification. A 2 ml culture of bacteria containing the recombinant plasmid was grown for 8 hr, then streaked onto solid media (e.g. 6 petri plates (100×15 mm) with 1.5% agarose in LB medium (Gibco-BRL, Gaithersburg, Md.) containing 200 μg/ml ampicillin), grown to confluence overnight, then scraped into 9 L of liquid media (Brain Heart Infusion media, Difco) containing ampicillin (200 μg/ml). The culture was grown until the $A_{600}$ was 1.0, IPTG added (1 mM final concentration), and the culture grown for an additional 2 hours.

Bacteria were recovered by centrifugation (7,930×g, 10 min), and lysed in 90 ml of 6M Guanidine-HCl, 0.1 M $Na_2HPO_4$, pH 8.0 for 1 hour with vigorous shaking. Insoluble material was removed by centrifugation (11,000× g, 10 min, 4° C.). The pH of the lysate was adjusted to pH 8.0, and the lysate applied to an 80 ml Nickel NTA agarose column (Qiagen, Chatsworth, Calif.) that had been equilibrated with 6 M Guanidine HCl, 100 mM $Na_2HPO_4$, pH 8.0. The column was sequentially washed with 6 M Guanidine HCl, 100 mM $Na_2HPO_4$, 10 mM Tris-HCl, pH 8.0, then 8 M urea, 100 mM $Na_2HPO_4$, pH 8.0, and finally 8 M urea, 100 mM sodium acetate, 10 mM Tris-HCl, pH 6.3. The column was washed with each buffer until the flow through had an $A_{280}$<0.05.

The recombinant protein, rLol p V, was eluted with 8 urea, 100 mM sodium acetate, 10 mM Tris-HCl, pH 4.5, and collected in 10 ml aliquots. The protein concentration of each fraction was determined by absorbance at $A_{280}$ and the peak fractions pooled. An aliquot of the collected recombinant protein was analyzed on SDS-PAGE (data not shown) according to the method in Sambrook et al., supra.

The first 9 liter preparation yielded 12 mg of rLol p V with approximately 60–70% purity. Purity of the preparation was determined by densitometry (Shimadzu Flying Spot Scanner, Shimadzu Scientific Instruments, Inc., Braintree, Mass.) of the coomassie-blue stained SDS-PAGE gel.

EXAMPLE 5

Cloning and Expression of Dac g V

*Dactylis glomerata* pollen was purchased from Greer Laboratories (Lenoir, N.C.). RNA was isolated as previously described in PCT/US92/05661 (WO93/01213) and polyA+ RNA was isolated using MICRO-FAST TRACK® mRNA isolation kit from Invitrogen (San Diego, Calif.). Double stranded cDNA was made with the BRL cDNA SYNTHESIS PLUS® kit (Gaithersburg, Md.). A cDNA library was made in lgt10 using the cDNA CLONING SYSTEM-lGT10® (Amersham, Arlington Heights, Ill.). The *D. glomerata* double stranded cDNA was ligated with adaptor arms, containing Eco RI, Bam HI, Kpn I and Nco I restriction sites and ligated into (lambda) gt10 vector arms using the manufacturer's suggested protocols. The library was packaged and titred also using the manufacturer's suggested protocols. The library was plated out and over 100,000 independent phage plaques were screened using random primed (RANDOM PRIMED DNA LABELING KIT®, Boehrninger Mannheim Corporation, Indianapolis, Ind.) or nick-translated probe [Sambrook J et al. Molecular Cloning: A Laboratory Manual. Cold Spring Harbor: Cold Spring Harbor Laboratory, 1989]. The library was screened with the 1.2 kb Lol p V clone 12R cDNA [Singh MB et al, *Proc Natl Acad Sci USA,* 1991; 88: 1384–1388].

There were many positive clones identified in the first screen. Several clones were picked using standard techniques [Sambrook J et al. Molecular Cloning: A Laboratory Manual. Cold Spring Harbor: Cold Spring Harbor Laboratory, 1989] and dilutions of high-titred phage stocks were re-screened using the same Lol p V clone 12R probe. The phage stocks were prepared using standard techniques [Sambrook J et al. Molecular Cloning: A Laboratory Manual. Cold Spring Harbor: Cold Spring Harbor Laboratory, 1989]. Positive clones were again picked, high-titred stocks prepared as before and serial dilutions were prepared for tertiary screening with the Lol p V clone 12R probe. Six phage clones, 228, 235, 236, 259, 267, and 285, were positive after this tertiary screening and high titred stocks were prepared as described [Sambrook J et al. Molecular Cloning: A Laboratory Manual. Cold Spring Harbor: Cold Spring Harbor Laboratory, 1989]. The cDNA inserts were isolated from the selected phage using standard techniques [Sambrook J et al. Molecular Cloning: A Laboratory Manual. Cold Spring Harbor: Cold Spring Harbor Laboratory, 1989]. The insert from clone 228 was approximately 500 base pairs (bp). The insert from clone 235 was approximately 1,000 bp. The insert from clone 236 was approximately 1200 bp. The insert from clone 259 was approximately 1,200 bp. The insert from clone 267 was approximately 1,000 bp. The insert from clone 285 was approximately 800 bp. The isolated inserts were cloned into appropriately digested pUC18 and/or pUC19 for subsequent analysis. The cDNA inserts were sequenced using the SEQUENASE® kits (USB, Cleveland, Ohio) based on the standard dideoxy chain termination method of Sanger et al. [Sanger F et al. *Proc Natl Acad Sci USA,* 1977; 74: 5460–5463].

Partial sequences for all of the clones were determined. All were found to contain Dac g V sequences by comparison with Lol p V clone 12R sequence (SEQ ID NO:2) [Ong EK et al. *Gene,* 1993; 134: 235–240]. The partial translated sequences of clones 235 and 236 were very similar to each other, although they started at different sites in the sequence (not shown), and appear to represent one isoform of Dac g V. The partial translated sequence of clone 259 was different from that of clones 235 and 236 and appear to represent a second isoform of Dac g V. The partial translated sequence of clone 259 is most homologous to the sequence of Lol p V clone 12R (SEQ ID NO:2) [Ong EK et al. *Gene* 1993; 134: 235–240]. The partial translated sequences of clones 235 and 236 are most closely homologous to the sequence of Lol p V clone 19R [Ong EK et al. *Gene* 1993; 134: 235–240].

Clone 259 was sequenced in its entirety. It was sequenced from both ends using standard forward and reverse primers (New England Biolabs, Beverly, Mass.). Subconstructs were prepared by digestion of isolated insert with Eco RI and Pst I and the fragments were cloned into appropriately digested pUC18 for internal sequencing. The Eco RI/Pst I insert that corresponded to the 5' portion of the Dac g V gene was isolated and further digested with Stu I or Sau 3A and Xho I and ligated into appropriately digested pUC19 for further sequence analysis. The nucleotide (SEQ ID NO:57) and deduced amino acid (SEQ ID NO:58) sequence of clone 259 is shown in FIG. 16. Nucleotides 1–25 correspond to adaptor sequence. The sequence ends with the poly A tract; the adaptor sequence is not shown at the 3' end of the sequence. The nucleotide sequence from 700 to 1181 is only preliminary and some bases may be misidentified. For example, nucleotide 712 has been tentatively identified as a "C". However, this is the third position of the codon encoding Gly 196 and the presence of another nucleotide at residue 712 would not change the predicted amino acid. It is difficult to sequence the Group V grass allergens due to their high GC content.

Clone 236 and 259 have been deposited with the ATCC.

As Group V allergens tend to have very conserved regions, the major T cell epitope containing peptides of Lol p V as described herein, are likely to be the major T cell epitopes of Dac g V, particularly where the regions are highly conserved between the related grasses.

What is claimed is:

1. A composition consisting of a combination of peptides selected from the group of combinations consisting of:

COMBINATION (a): LPIX-4 (SEQ ID NO:6), LPIX-5 (SEQ ID NO:7), LPIX-6 (SEQ ID NO:8), LPIX-16 (SEQ ID NO:18), LPIX-17 (SEQ ID NO:19), and LPIX-20 (SEQ ID NO:22);

COMBINATION (b): LPIX-4 (SEQ ID NO:6), LPIX-5 (SEQ ID NO:7), LPIX-6 (SEQ ID NO:8), LPIX-12 (SEQ ID NO:14), LPIX-16 (SEQ ID NO:18), LPIX-17 (SEQ ID NO:19), and LPIX-20 (SEQ ID NO:22);

LPIX-4 (SEQ ID NO:6), LPIX-5 (SEQ ID NO:7), LPIX-6 (SEQ ID NO:8), LPIX-17 (SEQ ID NO:19), and LPIX-20 (SEQ ID NO:22);

COMBINATION (c): LPIX-4 (SEQ ID NO:6), LPIX-5 (SEQ ID NO:7), LPIX-6 (SEQ ID NO:8), and LPIX-20 (SEQ ID NO:22);

COMBINATION (d): LPIX-4 (SEQ ID NO:6), LPIX-5 (SEQ ID NO:7), LPIX-6 (SEQ ID NO:8), LPIX-11 (SEQ ID NO: 13), LPIX-12 (SEQ ID NO:14), LPIX-16 (SEQ ID NO:18), LPIX-17 (SEQ ID NO:19), and LPIX-20 (SEQ ID NO:22);

COMBINATION (e): LPIX-4 (SEQ ID NO:6), LPIX-5 (SEQ ID NO:7), LPIX-6 (SEQ ID NO:8), LPIX-8 (SEQ ID NO: 10), LPIX-9 (SEQ ID NO: 11), LPIX-11 (SEQ ID NO: 13), LPIX-12 (SEQ ID NO:14), LPIX-16 (SEQ ID NO:18), LPIX-17 (SEQ ID NO:19), LPIX-19 (SEQ ID NO: 21), LPIX-20 (SEQ ID NO:22), LPIX-23 (SEQ ID NO:25), and LPIX-26 (SEQ ID NO:28);

COMBINATION (f): LPIX-4 (SEQ ID NO:6), LPIX-11 (SEQ ID NO: 13), LPIX-16 (SEQ ID NO:18), and LPIX-20 (SEQ ID NO:22);

COMBINATION (g): LPIX-4 (SEQ ID NO:6), LPIX-11 (SEQ ID NO: 13), LPIX-17 (SEQ ID NO:19), and LPIX-20 (SEQ ID NO:22);

LPIX-4 (SEQ ID NO:6), LPIX-16 (SEQ ID NO:18), LPIX-17 (SEQ ID NO:19), and LPIX-20 (SEQ ID NO:22);

COMBINATION (h): LPIX-5 (SEQ ID NO:7), LPIX-11 (SEQ ID NO: 13), LPIX-16 (SEQ ID NO:18), and LPIX-20 (SEQ ID NO:22);

COMBINATION (i): LPIX-5 (SEQ ID NO:7), LPIX-11 (SEQ ID NO: 13), LPIX-17 (SEQ ID NO:19), and LPIX-20 (SEQ ID NO:22);

COMBINATION (j): LPIX-5 (SEQ ID NO:7), LPIX-16 (SEQ ID NO:18), LPIX-17 (SEQ ID NO:19), and LPIX-20 (SEQ ID NO:22);

COMBINATION (k): LPIX-11 (SEQ ID NO: 13), LPIX-16 (SEQ ID NO:18), LPIX-17 (SEQ ID NO:19), and LPIX-20 (SEQ ID NO:22);

LPIX-4 (SEQ ID NO:6), LPIX-11 (SEQ ID NO: 13), and LPIX-20 (SEQ ID NO:22);

COMBINATION (l): LPIX-4 (SEQ ID NO:6), LPIX-16 (SEQ ID NO:18), and LPIX-20 (SEQ ID NO:22);

COMBINATION (m): LPIX-4 (SEQ ID NO:6), LPIX-17 (SEQ ID NO:19), and LPIX-20 (SEQ ID NO:22);

COMBINATION (n): LPIX-5 (SEQ ID NO:7), LPIX-11 (SEQ ID NO: 13), and LPIX-20 (SEQ ID NO:22);

COMBINATION (o): LPIX-5 (SEQ ID NO:7), LPIX-16 (SEQ ID NO:18), and LPIX-20 (SEQ ID NO:22);

COMBINATION (p): LPIX-11 (SEQ ID NO: 13), LPIX-16 (SEQ ID NO:18), and LPIX-20 (SEQ ID NO:22);

COMBINATION (q): LPIX-11 (SEQ ID NO: 13), LPIX-17 (SEQ ID NO:19), and LPIX-20 (SEQ ID NO:22);

COMBINATION (r): LPIX-16 (SEQ ID NO:18), LPIX-17 (SEQ ID NO:19), and LPIX-20 (SEQ ID NO:22);

COMBINATION (s): LPIX-5 (SEQ ID NO:7), LPIX-17 (SEQ ID NO:19), and LPIX-20 (SEQ ID NO:22);

COMBINATION (t): LPIX-4 (SEQ ID NO:6), LPIX-20 (SEQ ID NO:22);

COMBINATION (u): LPIX-5 (SEQ ID NO:7), and LPIX-20 (SEQ ID NO:22);

COMBINATION (v): LPIX-6 (SEQ ID NO:8), and LPIX-20 (SEQ ID NO:22);

COMBINATION (w): LPIX-11 (SEQ ID NO: 13), and LPIX-20 (SEQ ID NO:22);

COMBINATION (x): LPIX-12 (SEQ ID NO:14), and LPIX-20 (SEQ ID NO:22);

COMBINATION (y): LPIX-16 (SEQ ID NO:18), and LPIX-20 (SEQ ID NO:22); and

COMBINATION (z): LPIX-17 (SEQ ID NO:19), and LPIX-20 (SEQ ID NO:22).

2. A composition consisting of the composition of claim 1 and a pharmaceutically acceptable carrier or diluent.

* * * * *